(12) United States Patent
Ogawa et al.

(10) Patent No.: US 12,265,020 B2
(45) Date of Patent: Apr. 1, 2025

(54) FOOD SELECTION METHOD, FOOD SELECTION SYSTEM, ROBOT, NON-TRANSITORY COMPUTER-READABLE RECORDING MEDIUM STORING PROGRAM, AND COMPARISON METHOD

(71) Applicant: Panasonic Intellectual Property Management Co., Ltd., Osaka (JP)

(72) Inventors: Shohei Ogawa, Osaka (JP); Naomi Tomiyama, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 18/515,764

(22) Filed: Nov. 21, 2023

(65) Prior Publication Data

US 2024/0085316 A1 Mar. 14, 2024

Related U.S. Application Data

(63) Continuation of application No. 17/543,646, filed on Dec. 6, 2021, now Pat. No. 11,860,086, which is a
(Continued)

(30) Foreign Application Priority Data

Dec. 26, 2019 (JP) .................................. 2019-235971

(51) Int. Cl.
*G01N 21/31* (2006.01)
*G01J 3/28* (2006.01)
(Continued)

(52) U.S. Cl.
CPC .......... *G01N 21/314* (2013.01); *G01J 3/2823* (2013.01); *G01N 21/255* (2013.01);
(Continued)

(58) Field of Classification Search
CPC .. G01N 21/314; G01N 21/255; G01N 33/025; G01N 33/12; G01N 21/25;
(Continued)

(56) References Cited

U.S. PATENT DOCUMENTS

| 8,690,578 B1 | 4/2014 | Nusbaum et al. |
| 2015/0036138 A1 | 2/2015 | Watson et al. |

(Continued)

FOREIGN PATENT DOCUMENTS

| CN | 107835938 | 3/2018 |
| JP | 8-309292 | 11/1996 |

(Continued)

OTHER PUBLICATIONS

International Search Report (ISR) issued Feb. 22, 2021 in International (PCT) Application No. PCT/JP2020/045149.
(Continued)

*Primary Examiner* — Md M Rahman
(74) *Attorney, Agent, or Firm* — Wenderoth, Lind & Ponack, L.L.P.

(57) ABSTRACT

A food selection method includes obtaining one or more spectra corresponding to each of one or more foods, the one or more spectra being a result of measurement of each of the one or more foods using a spectral camera, comparing desire information indicating an attribute of a food desired by a user and a state of each of the one or more foods based on the one or more spectra, and selecting a food that suits the user's desire on a basis of a result of the comparing.

7 Claims, 17 Drawing Sheets

Related U.S. Application Data continuation of application No. PCT/JP2020/045149, filed on Dec. 4, 2020.

(51) Int. Cl.
- *G01N 21/25* (2006.01)
- *G01N 33/02* (2006.01)
- *G01N 33/12* (2006.01)
- *H04N 23/11* (2023.01)

(52) U.S. Cl.
CPC .......... *G01N 33/025* (2013.01); *G01N 33/12* (2013.01); *H04N 23/11* (2023.01); *G01J 2003/2826* (2013.01)

(58) Field of Classification Search
CPC ....... G01N 21/31; G01N 21/01; G01J 3/2823; G01J 2003/2826; H04N 23/11; G06Q 30/06; G06Q 50/10
USPC ........................................................ 356/402
See application file for complete search history.

(56) References Cited

U.S. PATENT DOCUMENTS

| | | |
|---|---|---|
| 2015/0379238 A1 | 12/2015 | Connor |
| 2016/0140870 A1 | 5/2016 | Connor |
| 2018/0136119 A1 | 5/2018 | Pi |
| 2018/0209901 A1 | 7/2018 | Schwartzer et al. |
| 2019/0259108 A1 | 8/2019 | Bongartz et al. |

FOREIGN PATENT DOCUMENTS

| | | |
|---|---|---|
| JP | 2002-63254 | 2/2002 |
| JP | 2013-073433 | 4/2013 |
| JP | 2014-75108 | 4/2014 |
| JP | 2018-84884 | 5/2018 |
| WO | 2017/176717 | 10/2017 |
| WO | 2019/102400 | 5/2019 |

OTHER PUBLICATIONS

English translation of Chinese Search Report dated Jan. 10, 2025 in related Chinese Patent Application No. 202080029152.8.

FIG. 2

| ID | ITEM | QUANTITY | SWEETNESS/ SOURNESS | PRIORITY | DESIRED DELIVERY DATE | DATE TO EAT |
|---|---|---|---|---|---|---|
| A00001 | TOMATOES | 3 | 2 | FRESHNESS | 2/1 | 2/2 |
| A00002 | MELONS | 1 | 1 | RIPENESS | 2/10 | 2/15 |
| A00003 | ORANGES | 20 | 4 | PRICE | 2/15 | 2/15 TO 2/28 |

| ITEM NUMBER | FRESHNESS | SWEETNESS/ SOURNESS | PRICE | RIGHT TIMING TO EAT | EXPIRATION DATE |
|---|---|---|---|---|---|
| TOMATOES α | FRESH | 3 | LIST PRICE | 2/3 TO 2/7 | 2/10 |
| TOMATOES β | SEMI-FRESH | 2 | 30% OFF | 1/30 TO 2/2 | 2/6 |
| TOMATOES γ | NON-FRESH | 4 | 50% OFF | 1/22 TO 1/28 | 2/4 |

FIG. 16

| RECOMMENDATION LEVEL | ITEM NUMBER | STOCK | PRICE (PER PIECE) | DELIVERY DATE | DETAILED INFORMATION | ORDER | |
|---|---|---|---|---|---|---|---|
| | | | | | | QUANTITY | PRICE |
| 1 | TOMATOES α | 5 | ¥70 | 2/3 | + | 3 | ¥350 |
| 2 | TOMATOES β | 2 | ¥50 | 2/2 | + | | |
| 3 | TOMATOES γ | 1 | ¥30 | 2/1 | + | | |
| | | | TOTAL | | | 3 | ¥350 |

| ID | ITEM | QUANTITY | SWEETNESS/ SOURNESS | COOKING METHOD | DESIRED DELIVERY DATE | DATE TO EAT |
|---|---|---|---|---|---|---|
| A00001 | TOMATOES | 3 | 2 | SALAD | 2/1 | 2/2 |
| A00002 | MELONS | 1 | 1 | RAW | 2/10 | 2/15 |
| A00003 | ORANGES | 20 | 4 | JUICE | 2/15 | 2/15 TO 2/28 |

| | ID | ITEM | QUANTITY | SWEETNESS/ SOURNESS | COOKING METHOD | DESIRED DELIVERY DATE | DATE TO EAT |
|---|---|---|---|---|---|---|---|
| USER'S DESIRES | A00001 | TOMATOES | 3 | 2 | SALAD | 2/1 | 2/2 |
| RECOMMENDATION BASED ON COOKING METHOD | A00011 | TOMATOES | 3 | 4 | SALAD | 2/1 | 2/2 |

| ITEM NUMBER | FRESHNESS | SWEETNESS/ SOURNESS | RIGHT TIMING TO EAT | DELIVERY FREQUENCY |
|---|---|---|---|---|
| TOMATOES α | FRESH | 3 | 2/1 TO 2/7 | BULK DELIVERY |
| TOMATOES β | FRESH | 3 | 2/8 TO 2/14 | |
| TOMATOES γ | FRESH | 3 | 2/15 TO 2/21 | |

FIG. 20

| ID | ITEM | QUANTITY | SWEETNESS/ SOURNESS | PRIORITY | DESIRED DELIVERY DATE | DATE TO EAT | DELIVERY METHOD (DESIRED TEMPERATURE) |
|---|---|---|---|---|---|---|---|
| A00001 | TOMATOES | 3 | 2 | FRESHNESS | 2/1 | 2/2 | REFRIGERATED |
| A00002 | MELONS | 1 | 1 | RIPENESS | 2/10 | 2/15 | REFRIGERATED |
| A00003 | ORANGES | 20 | 4 | PRICE | 2/15 | 2/15 TO 2/28 | UNREFRIGERATED |

FOOD SELECTION METHOD, FOOD SELECTION SYSTEM, ROBOT, NON-TRANSITORY COMPUTER-READABLE RECORDING MEDIUM STORING PROGRAM, AND COMPARISON METHOD

BACKGROUND

1. Technical Field

The present disclosure relates to a food selection method, a food selection system, a robot, a non-transitory computer-readable recording medium storing a program, and a comparison method.

2. Description of the Related Art

Provision of various services for a user based on spectral information (spectra) regarding products obtained from spectral cameras has been examined. Japanese Unexamined Patent Application Publication No. 2013-73433, for example, discloses a product processing apparatus that generates characteristic information indicating a state of a product on the basis of spectral information obtained by measuring the product using a hyperspectral camera and that sets a selling price of the product on the basis of the generated characteristic information.

SUMMARY

During these years, with the spread of networks, methods for selling products including foods via the Internet (electronic commerce (EC)) are becoming popular. Even in physical stores such as supermarkets, a sales method called an "online supermarket", in which products sold in a store are sold via the Internet, is used.

In such a sales method, a seller selects a food and sends the selected food to the user on the basis of a purchase instruction from the user. In this case, it is desirable that a state of the selected food matches the user's desire (e.g., a level of freshness).

One non-limiting and exemplary embodiment provides a food selection method with which a food closer to the user's desire can be selected.

In one general aspect, the techniques disclosed here feature a food selection method including obtaining one or more spectra corresponding to each of one or more foods, the one or more spectra being a result of measurement of each of the one or more foods using a spectral camera, comparing desire information indicating an attribute of a food desired by a user and a state of each of the one or more foods based on the one or more spectra, and selecting a food that suits the user's desire on a basis of a result of the comparing.

With the food selection method according to the aspect of the present disclosure and the like, a food closer to the user's desire can be selected.

It should be noted that this general or specific aspect may be implemented as an apparatus, a system, a method, an integrated circuit, a computer program, a non-transitory storage medium such as a compact disc read-only memory (CD-ROM), or any selective combination thereof. The computer program may be stored in a storage medium in advance or supplied to a storage medium over a wide-area communication network such as the Internet.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a diagram illustrating an example of a personal profile according to the embodiment;

FIG. 7 is a diagram illustrating an example of an item profile according to the embodiment;

FIG. 16 is a diagram illustrating an example of an order screen displayed on a display unit of the user terminal according to the embodiment;

FIG. 17 is a diagram illustrating an example of a personal profile according to a first modification of the embodiment;

FIG. 18 is a diagram illustrating an example of an item candidate profile displayed on the display unit of the user terminal according to the first modification of the embodiment;

FIG. 19 is a diagram illustrating an example of an item candidate profile displayed on the display unit of the user terminal according to a second modification of the embodiment; and FIG. 20 is a diagram illustrating an example of a personal profile according to a third modification of the embodiment.

DETAILED DESCRIPTION

Outline of Present Disclosure

Figure 1:
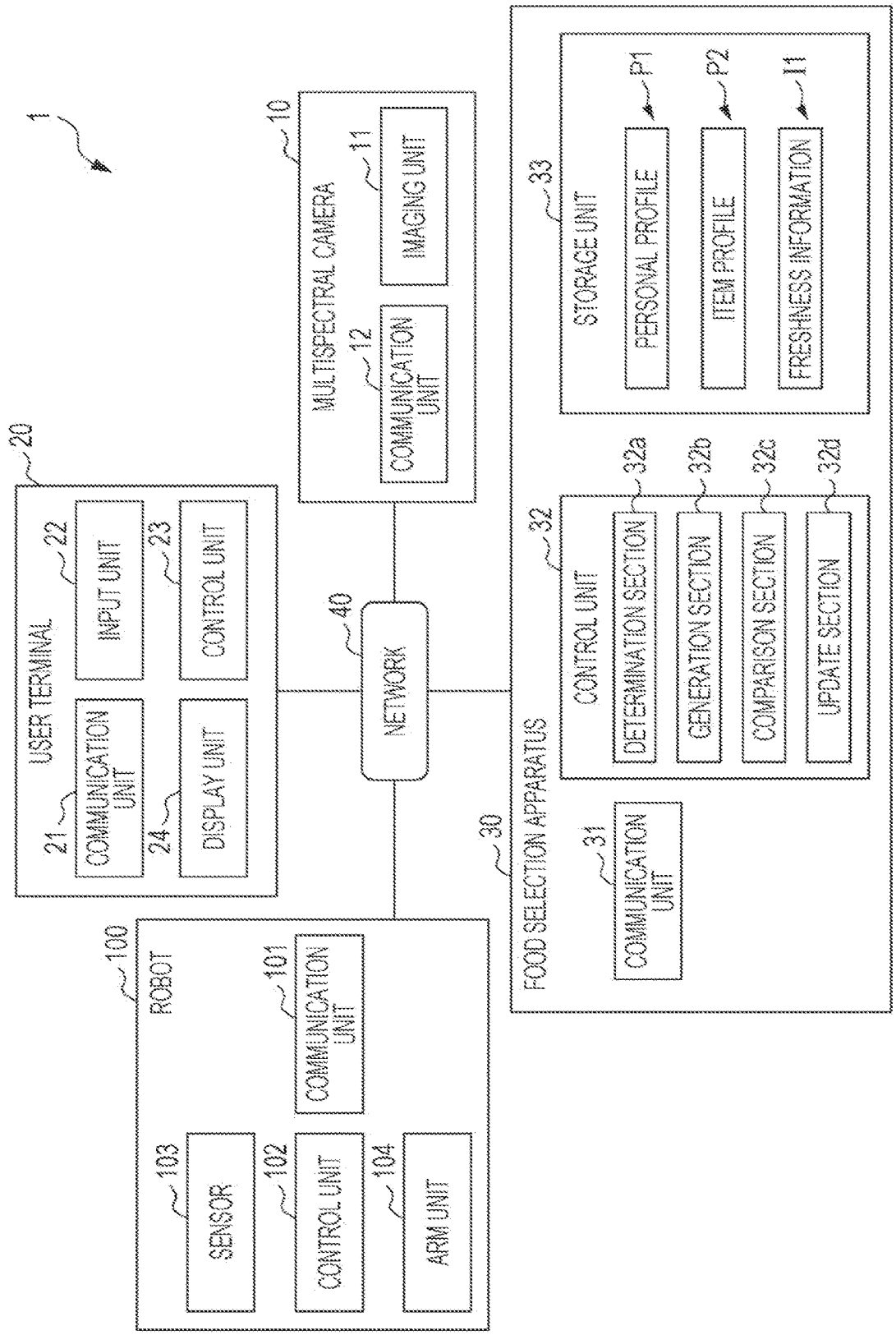
FIG. 1 is a block diagram illustrating the functional configuration of a food selection system according to an embodiment.

A food selection method according to an aspect of the present disclosure includes obtaining one or more spectra corresponding to each of one or more foods, the one or more spectra being a result of measurement of each of the one or more foods using a spectral camera, comparing desire information indicating an attribute of a food desired by a user and a state of each of the one or more foods based on the one or more spectra, and selecting a food that suits the user's desire on a basis of a result of the comparing.

The food selection method is thus used to select a food whose state based on a spectrum suits the user's desire (e.g., a desired level of freshness). When a spectrum obtained by measuring a food using a spectral camera are used, for example, a state of a food can be obtained more accurately than when a red, green, and blue (RGB) camera or the like is used. A food that suits the user's desire, therefore, can be selected more accurately. Consequently, with the food selection method according to the aspect of the present disclosure, a food closer to the user's desire can be selected.

In addition, for example, in the obtaining one or more spectra, two or more spectra may be obtained. In the selecting, two or more foods whose right timings to eat are different from each other may be selected as the food that suits the user's desire on a basis of the result of the comparing.

As a result, when the user is notified of two or more selected foods, for example, the user can select a food to be ordered among the two or more foods whose right timings to eat are different from each other. In addition, for example, by ordering two foods whose right timings to eat are different from each other, the user can use one of the two foods at the right timing to eat the food and the other food at the right timing to eat the other food. That is, the user can use both of the two foods in a state desired by the user. Foods even closer to the user's desire, therefore, can be selected. Use of a food may refer to eating of a food or cooking of a food.

In addition, for example, the food selection method may further include delivering a food ordered by the user. The desire information may include information regarding a frequency at which the user desires to receive the ordered food. In the delivering, if an order for the two or more foods is received, the two or more ordered foods may be delivered on a basis of the frequency.

As a result, since two or more foods can be delivered at delivery frequencies desired by the user, convenience of the food selection method improves.

In addition, for example, the food selection method may further include delivering a food ordered by the user. The desire information may include information regarding a temperature range at a time of delivery of the ordered food. In the delivering, the ordered food may be delivered using a delivery method according to the temperature range.

As a result, since a food can be delivered to the user within a temperature range desired by the user, the user need not take time to adjust the temperature of the food to a desired temperature. Since the food is delivered at the temperature desired by the user suitable for use, the user can, for example, use (e.g., eat) the food immediately after the delivery.

In addition, for example, the desire information may include a method for cooking a food. In the selecting, the food that suits the user's desire may be selected on a basis of the method for cooking a food and the state of each of the one or more foods.

As a result, with the food selection method, a food based on a cooking method can be selected. Since a food based on a cooking method desired by the user is selected, a food even closer to the user's desire can be selected.

In addition, for example, if there is no food that satisfies the user's desire in the selecting, a food close to the user's desire may be selected as the food that suits the user's desire.

As a result, even if there is no food that satisfies the user's desire, a food can be selected. When the user is notified of the selected food, for example, a food close to the user's desire can be presented to the user.

In addition, for example, in the selecting, the food that suits the user's desire may be selected using a robot.

As a result, the selected food can be automatically handled.

In addition, for example, the food selection method may further include notifying the user of food information regarding the selected food.

As a result, the user can be notified of food information.

In addition, for example, the food information may include prediction information regarding a state of the selected food.

As a result, the user can check prediction information and select a food to be ordered.

In addition, for example, the food information may include information indicating a right timing to eat the selected food, the information being based on the prediction information.

As a result, the user can check the food information and know a right timing to eat the food. For example, the user can determine, in consideration of the right timing to eat, whether to order the food and a quantity of the food to be ordered. That is, with the food selection method, the user can be helped to order a food that better suits his/her desire.

In addition, for example, the food information may include information indicating a discount rate of the selected food, the information being based on the prediction information.

As a result, the user can check the food information and know when a price of the food drops. For example, the user can order the food in accordance with a discount condition of the food. That is, with the food selection method, the user can be helped to order a food that better suits the user's desire.

In addition, for example, the food selection method may further include tentatively securing the food of which the user has been notified.

As a result, it becomes possible to inhibit other users from ordering the food of which the user has been notified.

In addition, for example, the food selection method may further include obtaining, from the user, feedback information regarding the food that has been delivered and updating the desire information on a basis of the feedback information.

As a result, the desire information better reflects the user's desire. When a food that suits the user's desire is selected using the desire information, a food that better suits the user's desire can be selected.

In addition, for example, the food may include at least one of a vegetable, a fruit, a meat, or a fish.

As a result, a food whose quality deteriorates quickly, such as a vegetable, a fruit, a meat, or a fish, and that is closer to the user's desire can be selected.

In addition, for example, the spectral camera may be a hyperspectral camera.

As a result, a more detailed spectrum can be obtained. For example, a more detailed spectrum than when a multispectral camera is used can be obtained. A state of a food based on such a spectrum, therefore, can be obtained more accurately. Consequently, a food even closer to the user's desire can be selected.

A food selection system according to another aspect of the present disclosure is a food selection system including a first obtainer that obtains one or more spectra corresponding to each of one or more foods, the one or more spectra being a result of measurement of each of the one or more foods using a spectral camera, a comparer that compares desire information indicating an attribute of a food desired by a user and a state of each of the one or more foods based on the one or more spectra, and a selector that selects a food that suits the user's desire on a basis of a result of the comparison.

As a result, the same advantageous effect as that produced by the food selection method can be produced.

A robot according to an aspect of the present disclosure is a robot including a second obtainer that obtains a result of comparison between desire information indicating an attribute of a food desired by a user and a state of each of one or more foods based on one or more spectra corresponding to the food, the one or more spectra being a result of measurement of each of the one or more foods using a spectral camera, a driver that moves the one or more foods, and a controller that controls the driver on a basis of the result of the comparison such that a food that suits the user's desire is selected.

As a result, with the robot according to the aspect of the present disclosure, a food even closer to the user's desire can be automatically selected.

A non-transitory computer-readable recording medium storing a program according to another aspect of the present disclosure is a non-transitory computer-readable recording medium storing a program for causing a computer to execute the food selection method.

As a result, the same advantageous effect as that produced by the food selection method can be produced.

A comparison method according to another aspect of the present disclosure is a comparison method including obtaining one or more spectra corresponding to each of one or more foods, the one or more spectra being a result of measurement of each of the one or more foods using a spectral camera and comparing desire information indicating an attribute of a food desired by a user and a state of each of the one or more foods based on the one or more spectra.

A spectrum of a food measured by a spectral camera includes more accurate information regarding a state of the food than an image of the food captured by an RGB camera. As a result, a food that suits the user's desire can be selected more accurately.

An embodiment will be specifically described hereinafter with reference to the drawings.

The following embodiment and modifications are general or specific examples. Values, shapes, materials, components, arrangement positions and connection modes of the components, steps, order of the steps, and the like are examples, and do not limit the present disclosure. Among the components described in the following embodiment, ones not mentioned in the independent claims will be described as optional components.

The drawings are schematic diagrams and not necessarily exact illustrations. In the drawings, substantially the same components are given the same reference numerals, and redundant description thereof might be omitted or simplified.

The values herein should not be strictly interpreted and may each have a certain range within which a meaning of the value remains essentially the same, namely a difference of, say, several percent.

Embodiment

A food selection system according to an embodiment and the like will be described hereinafter with reference to FIGS. 1 to 16.

1. Configuration of Food Selection System

First, a food selection system 1 that executes a food selection method according to the present embodiment will be described with reference to FIGS. 1 to 9. FIG. 1 is a block diagram illustrating the functional configuration of the food selection system 1 according to the present embodiment. The food selection system 1 is an example of a product selection system that selects products (e.g., foods) that suit the user's desires for, for example, an online supermarket. The food selection system 1 selects foods desired by the user using spectra (spectral information) obtained by measuring the foods using a multispectral camera 10.

An example where products are foods will be described hereinafter. Foods are products whose quality quickly deteriorates. The foods may be fresh foods and include, for example, at least a vegetable, a fruit, a meat, a fish, or milk. The foods may also include a processed food such as ham or sausages. In the following description, the foods will also be referred to as "items".

As illustrated in FIG. 1, the food selection system 1 includes the multispectral camera 10, a user terminal 20, a food selection apparatus 30, and a robot 100. The multispectral camera 10, the user terminal 20, and the food selection apparatus 30 are communicably connected to one another over a network 40. The network 40 is a wide area network (WAN) such as the Internet. The multispectral camera 10, the user terminal 20, and the food selection apparatus 30 are connected to one another over the network 40 (e.g., through relay apparatuses, which are not illustrated, provided at ends of the network 40), for example, such that the multispectral camera 10, the user terminal 20, and the food selection apparatus 30 can communicate with one another wirelessly.

The multispectral camera 10 obtains spectra of foods. The multispectral camera 10 measures a spectrum of a food when, for example, the food is harvested or delivered to a store. The multispectral camera 10 may measure a spectrum of a food at least once. The multispectral camera 10 may measure a spectrum of a food at a certain time (e.g., when the food is delivered to the store) or at certain time intervals. The certain time intervals may be appropriately determined in accordance with deterioration speed of the food and may be, for example, one day. When the multispectral camera 10 measures a spectrum of a food at certain time intervals, the multispectral camera 10 is provided, for example, at a place where the food is stored. A spectrum may indicate the intensity of light at each wavelength or absorbance at each wavelength.

The multispectral camera 10 may measure a spectrum of a food once or more than once at a certain timing. The multispectral camera 10 may measure spectra of a food at different positions of the food. A spectrum may include information for identifying a food subjected to measurement. Two or more multispectral cameras 10 may measure spectra of a food.

The multispectral camera 10 includes an imaging unit 11 and a communication unit 12.

The imaging unit 11 measures a spectrum of a food and includes, for example, an optical system, a spectrometer, and a detector, which are not illustrated. The optical system includes a lens, for example, and has a function of guiding incident light. The spectrometer includes a grating (diffraction grating), for example, and has a function of continuously splitting incident light for each of certain bands (e.g., for each of certain wavelengths). The detector includes light-receiving elements such as photosensors (e.g., line photosensors) and has a function of detecting the intensity of light beams obtained as a result of the splitting. A spectrum of a food can thus be obtained.

The communication unit 12 is a communication circuit (communication module) for communicating with other apparatuses over the network 40 such as the Internet. In the present embodiment, the communication unit 12 communicates with at least the food selection apparatus 30.

The multispectral camera 10 may further include a light source that emits light onto foods. The light source emits light in a wavelength band with which at least either freshness or ripeness (e.g., a freshness level or a ripeness level, which will be described later) can be determined. The light source may emit visible light or light including infrared light (e.g., near-infrared light).

A spectral camera included in the food selection system 1 is not limited to the multispectral camera 10, and may be a hyperspectral camera or an ultra-spectral camera, instead. Here, the multispectral camera 10 refers to a spectral camera capable of obtaining spectra in a maximum of 10 bands, the hyperspectral camera refers to a spectral camera capable of obtaining spectra in about 100 to 200 bands, and the ultra-spectral camera refers to a spectral camera capable of obtaining spectra in 1000 bands or more. The spectral camera in the present disclosure does not include an RGB camera that obtains wavelength information in three bands.

The spectral camera included in the food selection system 1 is desirably a hyperspectral camera in view of appropriately selecting foods that satisfy the user's desires.

The user terminal 20 is a terminal apparatus owned by a user who purchases foods. The user terminal 20 may be a mobile terminal such as a smartphone, a tablet terminal, or a wearable terminal or may be a desktop and/or laptop personal computer. The user terminal 20 includes a communication unit 21, an input unit 22, a control unit 23, and a display unit 24.

The communication unit 21 is a communication circuit (communication module) for communicating other apparatuses over the network 40 such as the Internet. In the present embodiment, the communication unit 21 communicates with the food selection apparatus 30 over the network 40. The communication unit 21 outputs, to the food selection apparatus 30 over the network 40, a personal profile (e.g., a personal profile P1 illustrated in FIG. 2) indicating attributes of foods desired by the user. The communication unit 21 obtains information based on a result of selection of foods from the food selection apparatus 30 over the network 40.

The input unit 22 is a user interface for receiving an operation for selecting a food from the user. For example, the input unit 22 receives, from the user, an operation for generating a personal profile, an operation for purchasing foods, and the like. The input unit 22 is achieved by hardware keys (hardware buttons), slide switches, a touch panel, or the like. For example, the input unit 22 may receive such operations from the user by sound, gesture, or the like.

The control unit 23 is a control device that controls the components of the user terminal 20. For example, the control unit 23 obtains the user's desires on foods through the input unit 22, generates a personal profile on the basis of the obtained desires, and outputs the generated personal profile to the food selection apparatus 30 through the communication unit 21. The control unit 23 also obtains information based on a result of selection from the food selection apparatus 30 through the communication unit 21 and displays the obtained information on the display unit 24.

The control unit 23 is achieved, for example, by a microcomputer or a processor.

A personal profile generated by the control unit 23 will be described with reference to FIG. 2. FIG. 2 is a diagram illustrating an example of the personal profile P1 according to the present embodiment. The personal profile P1 is an example of desire information.

As illustrated in FIG. 2, the personal profile P1 includes "ID", "item", "quantity", "sweetness/sourness", "priority", "desired delivery date", and "date to eat".

"ID" is identification information for identifying a food. "ID" is set for each food, for example, but may be set for each variety of food.

"Item" indicates a name of a food to be purchased by the user. In FIG. 2, the user is planning to purchase tomatoes, a melon, and oranges.

"Quantity" indicates a quantity of a food to be purchased by the user.

"Sweetness/sourness" is an item indicating the user's preference about taste and, in the example illustrated in FIG. 2, indicates a level of sweetness and sourness of a food desired by the user. In FIG. 2, "1" indicates highest sweetness and "5" indicates highest sourness, that is, five levels of sweetness and sourness are set. It can be seen from FIG. 2 that the user desires a sweet melon and relatively sour oranges. The personal profile P1 need not necessarily include "sweetness/sourness" insofar as the personal profile P1 includes information regarding the user's preference about taste. Any personal profile P1 including information indicating the user's preference about taste that can be estimated from spectra, that is, for example, information indicating the user's preference with respect to at least sweetness, bitterness, saltiness, or sourness, may be used.

"Priority" indicates an item that the user puts priority in purchase of a food. The item may be "freshness", "ripeness", or "price", but is not limited to these. When the user selects "freshness", freshness takes priority in satisfying the user's desire among freshness, ripeness, and price. When the user selects "ripeness", ripeness takes priority in satisfying the user's desire among freshness, ripeness, and price. When the user selects "price", price takes priority in satisfying the user's desire among freshness, ripeness, and price. The user's desire on "price" may be satisfied if, for example, a desired price is met or a desired discount rate is applied.

It can be seen from FIG. 2 that the user puts priority on freshness for tomatoes, ripeness for a melon, price for oranges. Items used for "priority" are not limited to these three, and any items that can be estimated from a spectrum may be used. Items used for "priority" may include taste (e.g., sweetness/sourness).

"Desired delivery date" indicates a date on which the user desires to receive a food. A desired delivery date may be a specific date or a period. "Desired delivery date" may include information regarding a time period in which the user desires to receive a food.

"Date to eat" indicates a date on which the user is planning to eat a dish that uses a food. "Date to eat" may be a specific date or a period. "Date to eat" may be "date to cook", instead.

"Quantity", "sweetness/sourness", "priority", "desired delivery date", "date to eat", and the like are an example of attributes desired by the user.

"Sweetness/sourness" and "priority" in the personal profile P1 may be input every time the user generates a personal profile P1 or automatically set on the basis of information such as an order history.

FIG. 1 will be referred to again. The display unit 24 is a display panel that displays the personal profile P1, information based on a result of selection performed by the food selection apparatus 30, a screen for ordering foods, and the like. The display unit 24 is achieved by a liquid crystal panel, for example, but may be achieved by another display panel such as an organic electroluminescent (EL) panel, instead. The display unit 24 may include a backlight.

The food selection apparatus 30 is an information processing apparatus that performs a process for selecting a food that suits the user's desires on the basis of desire information indicating attributes of foods desired by the user and spectra obtained from the multispectral camera 10. More specifically, the food selection apparatus 30 compares the desire information and states of foods based on the spectra and selects foods that suit the user's desires on the basis of a result of the comparison. A food suits the user's desires if the food satisfies at least one of the user's desires.

The food selection apparatus 30 includes a communication unit 31, a control unit 32, and a storage unit 33. The food selection apparatus 30 is an apparatus (e.g., a system) provided at a store such as an online supermarket.

The communication unit 31 is a communication circuit (communication module) for communicating with other apparatuses over the network 40 such as the Internet. In the present embodiment, the communication unit 31 communicates with the multispectral camera 10 and the user terminal 20. The communication unit 31 functions as a first obtainer that obtains spectra of foods from the multispectral camera 10 over the network 40 and that obtains the personal profile P1 from the user terminal 20 over the network 40. The communication unit 31 also functions as an outputter that outputs information based on a result of selection performed by the food selection apparatus 30 to the user terminal 20 over the network 40 and the like.

The communication unit 31 may be communicably connected to apparatuses other than those described above over the network 40. The communication unit 31 may communicate, for example, with a sensor apparatus that measures a storage environment of a place storing foods. The storage environment includes, for example, at least temperature or humidity.

The control unit 32 is a control device that controls the components of the food selection apparatus 30. The control unit 32 performs the process for selecting a food that suits the user's desires on the basis of spectra obtained from the multispectral camera 10 and the personal profile P1 of the user obtained from the user terminal 20. The control unit 32 is achieved, for example, by a microcomputer or a processor.

The control unit 32 includes a determination section 32a, a generation section 32b, a comparison section 32c, and an update section 32d.

The determination section 32a determines states of foods on the basis of spectra obtained from the multispectral camera 10. The determination section 32a determines freshness and/or ripeness of foods on the basis of the spectra obtained from the multispectral camera 10. In the present embodiment, the determination section 32a determines both the freshness and ripeness of foods. Since the determination section 32a determines states of foods on the basis of spectra, the determination section 32a can determine the states of the foods in a noncontact manner.

First, determination of freshness (freshness level) of a food will be described. The determination section 32a determines a freshness level of a food on the basis of a spectrum obtained from the multispectral camera 10. More specifically, the determination section 32a determines the freshness level of the food on the basis of the amount of a main ingredient (e.g., the amount of water) that is obtained from the spectrum and that changes over time. In a case where the determination section 32a calculates amounts of water on the basis of spectra, the determination section 32a determines a freshness level of a food whose freshness is to be determined on the basis of the amount of water based on a spectrum of the food and a reference amount of water based on a reference spectrum. In the following description, a spectrum of a food whose freshness is to be determined will be referred to as a "target spectrum", and the amount of water based on a target spectrum will be referred to as a "target amount of water".

A reference spectrum is a spectrum that serves as a reference for determining a freshness level. A reference spectrum is obtained in advance and, for example, stored in the storage unit 33. For example, a reference spectrum is obtained by measuring a fresh food using the multispectral camera 10. A reference amount of water is an amount of water calculated on the basis of the reference spectrum and may be a maximum value of the amount of water of a food.

The determination section 32a determines a target amount of water divided by a reference amount of water as a freshness index, for example, and determines a current freshness level on the basis of the freshness index. If the freshness index is higher than or equal to 0.5, the determination section 32a determines a freshness level of a food as "fresh". If the freshness index is higher than or equal to 0.25 or lower than 0.5, the determination section 32a determines a freshness level of a food as "semi-fresh". If the freshness index is lower than 0.25, the determination section 32a determines a freshness level of a food as "non-fresh". The food selection apparatus 30 can thus obtain a freshness level of a food when the food is harvested or delivered to the store. The determination section 32a may then store, in the storage unit 33, freshness information including the freshness index and the freshness level.

The determination section 32a may make the above determination on the basis of a light reflectance in a certain wavelength band of a target spectrum obtained from the multispectral camera 10, instead. The determination section 32a may make the above determination on the basis of a light reflectance in a certain wavelength band based on a target spectrum of a food and a reference light reflectance in a certain wavelength band based on a reference spectrum corresponding to the food, instead. The certain wavelength band is not particularly limited insofar as changes in the amount of water can be measured therein. The certain wavelength band may be set for each food. A reflectance can be calculated from a spectrum of light emitted from the light source and a spectrum of reflected light measured by the multispectral camera 10.

Thresholds for the freshness index and definitions of freshness levels, which are used to determine the freshness level, may be different or the same between foods. The thresholds for the freshness index and the definitions of the freshness levels may be different between users or set by the user using the user terminal 20, instead.

A method for determining the freshness level from a target spectrum is not limited to the above example, and any known technique may be used. For example, the determination section 32a may determine the freshness level on the basis of color information indicating a color of a surface of a food, instead. The color information can be obtained on the basis of a target spectrum. Alternatively, for example, the determination section 32a may determine the freshness level on the basis of an absolute value of the amount of water based on a target spectrum without using a reference spectrum.

Next, determination of ripeness (ripeness level) of a food will be described. The determination section 32a determines a ripeness level of a food on the basis of a spectrum obtained from the multispectral camera 10. More specifically, the determination section 32a determines the ripeness level of the food on the basis of the amount of a main ingredient (e.g., the amount of reflection) that is obtained from the spectrum and that changes over time. In a case where the determination section 32a calculates amounts of reflection on the basis of spectra, the determination section 32a determines a ripeness level of a food whose freshness is to be determined on the basis of the amount of reflection based on a spectrum of the food and a reference amount of reflection based on a reference spectrum of the food. In the following description, a spectrum of a food whose ripeness is to be determined will be referred to as a "target spectrum", and the amount of reflection based on the target spectra will be referred to as a "target amount of reflection".

A reference spectrum is a spectrum that serves as a reference for determining a ripeness level. A reference spectrum is obtained in advance and, for example, stored in the storage unit 33. For example, a reference spectrum is obtained by measuring barium sulfate as a standard white sample using the multispectral camera 10. A reference amount of reflection is, for example, an amount of reflection of the standard white sample. For example, a reference spectrum may be obtained by measuring a fresh food using the multispectral camera 10, instead.

The determination section 32a determines a target amount of reflection divided by a reference amount of reflection as a ripeness index, for example, and determines a current ripeness level on the basis of the ripeness index. If the ripeness index is higher than or equal to 0.5, the determination section 32a determines a ripeness level of a food as "ripe". If the ripeness index is higher than or equal to 0.25 or lower than 0.5, the determination section 32a determines a ripeness level of a food as "semi-ripe". If the ripeness index is lower than 0.25, the determination section 32a determines a ripeness level of a food as "unripe". The food selection apparatus 30 can thus obtain a ripeness level of a food when the food is harvested or delivered to the store. The determination section 32a may then store, in the storage unit 33, ripeness information including the ripeness index and the ripeness level.

Thresholds for the ripeness index and definitions of ripeness levels, which are used to determine the ripeness level, may be different or the same between foods. The thresholds for the ripeness index and the definitions of the ripeness levels may be different between users or set by the user using the user terminal 20, instead.

A method for determining the ripeness level from a target spectrum is not limited to the above example, and any known technique may be used. For example, the determination section 32a may determine the ripeness level on the basis of color information indicating a color of a surface of a food, instead. The color information can be obtained on the basis of a target spectrum.

In the present embodiment, the determination section 32a also predicts freshness and ripeness. The determination section 32a predicts freshness and ripeness for, for example, each of days from present time (e.g., a time at which a spectrum is measured). In other words, the determination section 32a predicts a freshness index and a ripeness index for, for example, each of days from present time (e.g., a time at which a spectrum is measured).

For example, the determination section 32a predicts a freshness index and a ripeness index of a food on the basis of a current freshness index and a current ripeness index of the food and transition models indicating how the freshness index and the ripeness index change over time. The transition models are obtained in advance, for example, and stored in the storage unit 33. For example, the storage unit 33 may store a transition model for each of freshness levels and each of ripeness levels. The storage unit 33 may store a transition model for each of storage environments of a food.

Figure 3:
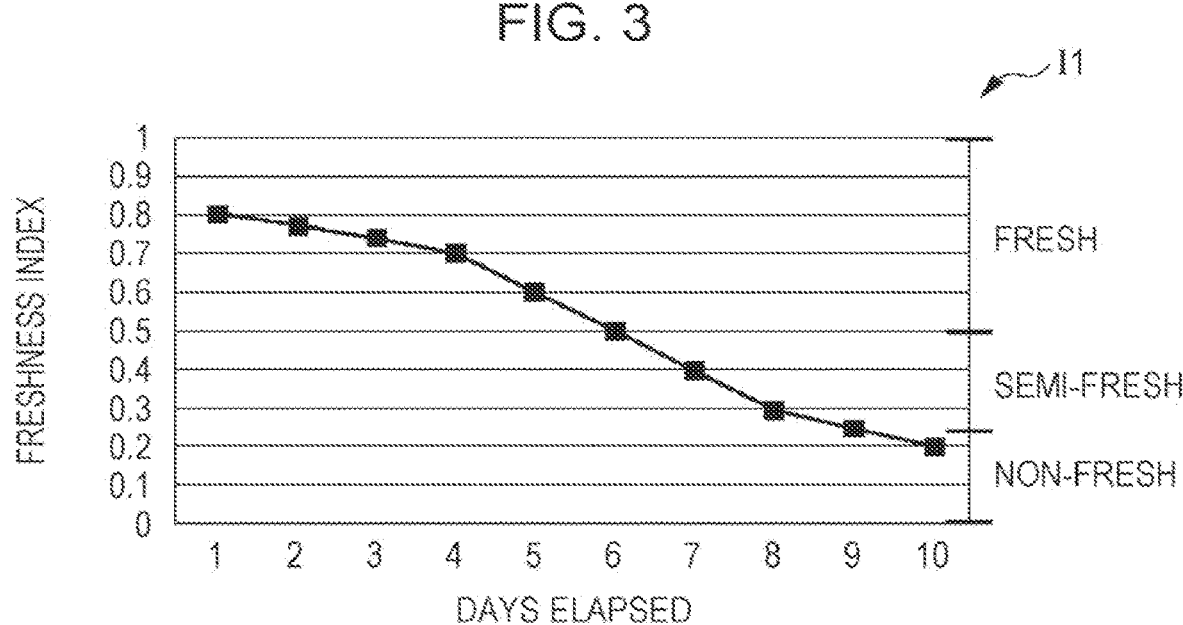
FIG. 3 is a diagram illustrating an example of freshness information according to the embodiment.

When a freshness level of a food is "fresh", for example, the determination section 32a may estimate changes (transition) in a freshness index of the food on the basis of a current freshness index of the food and a transition model corresponding to the freshness level "fresh". FIG. 3 is a diagram illustrating an example of freshness information 11 according to the present embodiment. More specifically, FIG. 3 is a diagram illustrating an example of a relationship between a result of prediction of the freshness index and the freshness level. In FIG. 3, a horizontal axis represents days elapsed and a vertical axis represents the freshness index (a ratio of the amount of water in the present embodiment). The horizontal axis may represent dates, instead.

As illustrated in FIG. 3, the determination section 32a predicts the freshness index of a food on second and later days, for example, on the basis of the freshness index on a first day and the transition model corresponding to the freshness level "fresh". Since the food selection apparatus 30 can obtain a predicted value of the freshness index for each of days from the present time, a relationship between the days elapsed and the freshness levels can be obtained. In the example of FIG. 3, the freshness level is "fresh" until a sixth day, "semi-fresh" from a seventh day to a ninth day, and "non-fresh" on a tenth day and later.

The determination section 32a can also determine right timing to eat a food (refer to FIG. 7, which will be referred to later), for example, on the basis of a result of prediction of the freshness index. The determination section 32a may also determine an expiration date (refer to FIG. 7, which will be referred to later) of the food on the basis of the result of prediction of the freshness index. The determination section 32a may store the freshness information 11 in the storage unit 33.

Figure 4:
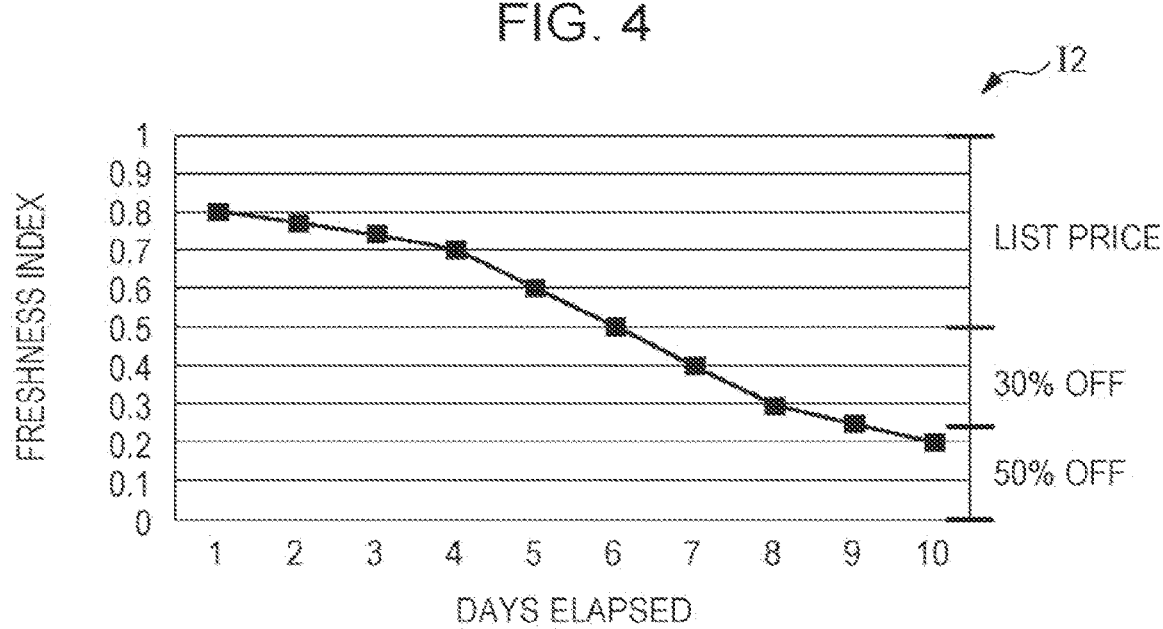
FIG. 4 is a diagram illustrating an example of discount information according to the embodiment.

The determination section 32a may also determine a discount rate applied to a selling place (e.g., a list price) of a food on the basis of the result of prediction of the freshness index. FIG. 4 is a diagram illustrating an example of discount information 12 according to the present embodiment. More specifically, FIG. 4 is a diagram illustrating an example of a relationship between the freshness index and the discount rate. In FIG. 4, a horizontal axis represents days elapsed and a vertical axis represents the freshness index and the discount rate. The horizontal axis may represent dates, instead.

As illustrated in FIG. 4, the determination section 32a may determine the discount rate for a food in accordance with the current freshness index on the basis of the relationship between the freshness index and the discount rate. The result of prediction of the freshness index is obtained, for example, on a first day. On a seventh day, the determination section 32a may determine that the discount rate is "30% off" on the basis of the relationship illustrated in FIG. 4. It can also be said, for example, that the determination section 32a predicts a state of a food at the present time (e.g., on the seventh day) on the basis of a spectrum obtained in the past (e.g., on a zeroth day) and applies a discount rate corresponding to the predicted state of the food to a price. The determination section 32a may store the discount information 12 in the storage unit 33.

FIGS. 3 and 4 illustrate an example where the discount rate is "0 (list price)" for the freshness level "fresh", "30% off" for the freshness level "semi-fresh", and "50% off" for the freshness level "non-fresh". That is, although the freshness level and the discount rate are set in one-to-one correspondence in FIGS. 3 and 4, a method for setting the discount rate is not limited to this. The discount rate may be set regardless of the freshness level, instead. For example, the discount rate may be set in one-to-one correspondence with the ripeness level.

Figure 5:
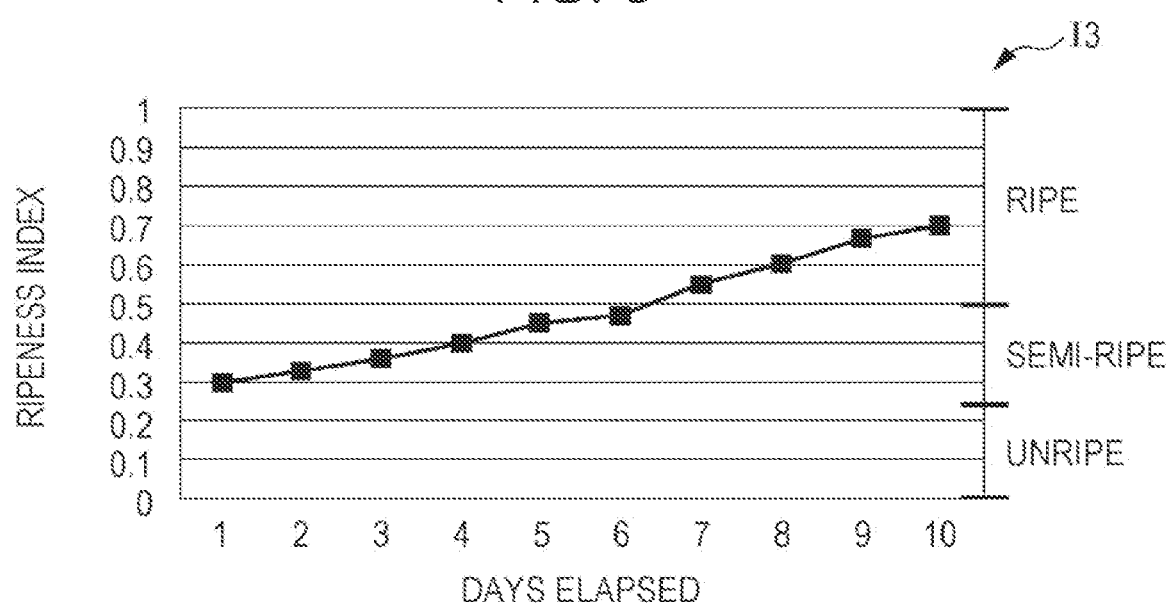
FIG. 5 is a diagram illustrating an example of ripeness information according to the embodiment.

Alternatively, when a ripeness level of a food is "semi-ripe", for example, the determination section 32a may estimate changes in the ripeness index of the food on the basis of the current ripeness index of the food and a transition model corresponding to the ripeness level "semi-ripe". FIG. 5 illustrates an example of ripeness information 13 according to the present embodiment. More specifically, FIG. 5 is a diagram illustrating an example of a relationship between a result of prediction of the ripeness index and the ripeness level. In FIG. 5, a horizontal axis represents days elapsed, and a vertical axis represents the ripeness index (a ratio of the amount of reflection in the present embodiment). The horizontal axis may represent dates, instead.

As illustrated in FIG. 5, the determination section 32a predicts the ripeness index of a food on second and later days on the basis of the ripeness index on a first day and the transition model corresponding to the ripeness level "semi-ripe". Since the food selection apparatus 30 can obtain the ripeness index for each of days from the present time, the food selection apparatus 30 can obtain a relationship between the days elapsed and the ripeness level. In the example illustrated in FIG. 5, the ripeness level is "semi-ripe" until a sixth day and "ripe" on a seventh day and later.

Alternatively, the determination section 32a may determine a right timing to eat a food (refer to FIG. 7, which will be referred to later), for example, on the basis of a result of prediction of the ripeness index. The determination section 32a may also determine an expiration date (refer to FIG. 7, which will be referred to later) of the food on the basis of the result of prediction of the ripeness index. The determination section 32a may store the ripeness information 13 in the storage unit 33.

In the present embodiment, the determination section 32a also determines a sweetness/sourness level (levels "1" to "5" in the present embodiment) of a food on the basis of a spectrum. The determination section 32a calculates, for example, the amount of so-called "sugars" contained, such as sucrose (so-called "sugar"), fructose, invert sugar, and glucose from a spectrum and then calculates a sweetness index on the basis of the calculated amount of sugars contained. The sweetness index is calculated, for example, by dividing the amount of sugars contained by a reference amount of sugars contained. In this case, a spectrum includes information regarding a wavelength at which, or a wavelength band in which, a reflectance differs depending on the amount of sugars contained. For example, the determination section 32a calculates the amount of citric acid contained in a food from a spectrum and then calculates a sourness index on the basis of the calculated amount of citric acid contained. The sourness index is calculated, for example, by dividing the amount of citric acid contained by a reference amount of citric acid contained. In this case, a spectrum includes information regarding a wavelength at which, or a wavelength band in which, a reflectance differs depending on the amount of citric acid contained. A method for calculating the sweetness index and the sourness index of a food is not limited to the above example, and any known technique may be used insofar as a spectrum of a food is used.

Figure 6:
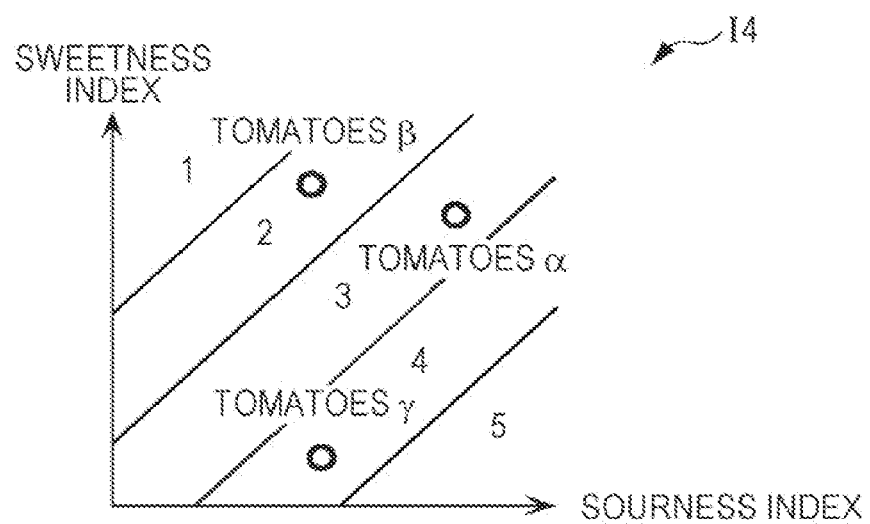
FIG. 6 is a diagram illustrating an example of taste information according to the embodiment.

The determination section 32a determines a sweetness/sourness level of a food on the basis of a calculated sweetness index, a calculated sourness index, and a relationship between the sweetness index and the sourness index of a food illustrated in FIG. 6. FIG. 6 is a diagram illustrating an example of taste information 14. More specifically, FIG. 6 is a diagram illustrating sweetness/sourness levels of foods. Values "1" to "5" illustrated in FIG. 6 indicate sweetness/sourness levels. The relationship between the sourness index, the sweetness index, and the sweetness/sourness level illustrated in FIG. 6 is set in advance, for example, and stored in the storage unit 33.

As illustrated in FIG. 6, for example, a sweetness index and a sourness index of tomatoes α is well balanced, and a sweetness/sourness level is "3". In this case, the determination section 32a determines the sweetness/sourness level of tomatoes α to be "3". The determination section 32a also determines sweetness/sourness levels of tomatoes β and γ to be "2" and "4", respectively.

FIG. 1 will be referred to again. The generation section 32b generates various pieces of information for selecting foods suitable for the user. The generation section 32b generates item profiles, which are food management information on a side of a store such as an online supermarket, on the basis of spectra obtained through the communication unit 31. The generation section 32b also generates advertisements (e.g., online advertisements) for promoting foods. The advertisements generated by the generation section 32b will be described later (e.g., refer to FIGS. 15 and 16). The generation section 32b may store the generated item profiles and advertisements in the storage unit 33.

The generation section 32b generates an item profile, for example, on the basis of a result of a determination made by the determination section 32a. FIG. 7 is a diagram illustrating an example of an item profile P2 according to the present embodiment.

As illustrated in FIG. 7, the item profile P2 includes "item number", "freshness", "sweetness/sourness", "price", "right timing to eat", and "expiration date". The item profile P2 may also include "ripeness" or the like.

"Item number" indicates identification information for identifying different types of food (item). The food may be "tomatoes", "melons", "oranges", or the like. The types may be different varieties of food (e.g., tomatoes) or different harvest times. In FIG. 7, three types of tomatoes, namely "tomatoes α", "tomatoes β", and "tomatoes γ", are stored as the food "tomatoes".

"Freshness" indicates a freshness level of a food. The freshness level may be "fresh", "semi-fresh", or "non-fresh", but is not limited to these. "Freshness" indicates, for example, a current freshness level of a food. "Freshness" can be obtained on the basis of a result of prediction (e.g., refer to FIG. 3) obtained by the determination section 32a.

"Sweetness/sourness" indicates a sweetness/sourness level of a food. "Sweetness/sourness" indicates, for example, a current sweetness/sourness level of a food.

"Sweetness/sourness" can be obtained on the basis of results of determinations (e.g., refer to FIG. 6) obtained by the determination section 32a.

"Price" indicates a current price of a food. "Price" is set, for example, in accordance with "freshness" or the like. "Price" can be obtained on the basis of a result of a determination (e.g., refer to FIG. 4) obtained by the determination section 32a.

"Right timing to eat" indicates a period of time when it is desirable to eat a food. "Right timing to eat" is set, for example, on the basis of "freshness" or the like. More specifically, "right timing to eat" is set on the basis of a result of prediction of "freshness".

"Expiration date" indicates a date until which a food can be safely consumed. "Expiration date" may be set on the basis of a result of prediction of "freshness", or a predetermined date may be set.

The generation section 32b may generate an item profile P2 that suits the user's preference. The generation section 32b may set "right timing to eat" on the basis of information in the personal profile P1, instead. That is, "right timing to eat" may be set for each user in accordance with the user's preference. If it is determined that a freshness level desired by the user based on the personal profile P1 is "fresh" and the determination section 32a determines, on the basis of the freshness information 11, that a period of time for which the freshness level remains at "fresh" is "right timing to eat" for the user, for example, the generation section 32b may generate the item profile P2 on the basis of the result of determination.

The comparison section 32c compares states of foods included in the personal profile P1 and the item profile P2 to determine whether the item profile P2 includes foods that suit the user's desires.

The update section 32d updates the various pieces of information stored in the storage unit 33. For example, the update section 32d updates items in the personal profile P1 stored in the storage unit 33 relating to the user's preference on the basis of feedback from the user about purchased foods.

The storage unit 33 is a storage device storing information used to perform the process for selecting a food. The storage unit 33 stores the personal profile P1, the item profile P2, and information regarding states of foods (e.g., the freshness information 11). The information regarding states of foods may include the discount information 12 and/or the ripeness information 13 instead of, or in addition to, the freshness information 11. The storage unit 33 may be, for example, a semiconductor memory.

Figure 8:
FIG. 8 is a diagram illustrating another example of the personal profile according to the embodiment.

The personal profile P1 is information including attributes, desired by the user, of certain foods obtained from the user terminal 20. The storage unit 33 may store a personal profile P3 illustrated in FIG. 8 instead of the personal profile P1. FIG. 8 is a diagram illustrating an example of the personal profile P3 according to the present embodiment.

As illustrated in FIG. 8, the personal profile P3 is, for example, information based on the personal profile P1 obtained from the user terminal 20. The personal profile P3 is, for example, information obtained by editing the personal profile P1 for each item. "Priority" may include, for example, order of priority of "freshness", "sweetness/sourness", and "price".

The freshness information 11 is information including freshness indices and freshness levels of foods and may include, for example, the result of prediction of the freshness index illustrated in FIG. 3. The discount information 12 is information including freshness indices and discount rates and may include, for example, the result of prediction of the discount rate illustrated in FIG. 4. The ripeness information 13 is information including ripeness indices and ripeness levels of foods and may include, for example, the result of prediction of the ripeness index illustrated in FIG. 5.

The robot 100 is an apparatus that handles foods. The robot 100 performs an operation for selecting a food that suits the user's desires on the basis of a result of comparison performed by the comparison section 32c. In the present embodiment, the robot 100 sorts out foods on the basis of spectra. The robot 100 includes a communication unit 101, a control unit 102, a sensor 103, and an arm unit 104.

The communication unit 101 is a communication circuit (communication module) for communicating with other apparatuses over the network 40 such as the Internet. In the present embodiment, the communication unit 101 communicates with at least the food selection apparatus 30. The communication unit 101 obtains, from the food selection apparatus 30 over the network 40, a result of comparison between desire information indicating attributes of foods desired by the user and a state of each of one or more foods based on one or more spectra corresponding to the food, the one or more spectra being a result of measuring each of the one or more foods using the multispectral camera 10. The communication unit 101 functions as a second obtainer.

The control unit 102 is a control device that controls the components of the robot 100. For example, the control unit 102 controls the arm unit 104 in such a way as to select foods that suit the user's desires on the basis of the result of comparison. The control unit 102 moves foods to positions according to the result of comparison, for example, by controlling the arm unit 104 on the basis of the result of comparison.

The control unit 102 moves (e.g., rotates) the arm unit 104 by controlling motors provided at joints of the arm unit 104.

The sensor 103 is a camera, for example, and senses surrounding conditions of the robot 100. The sensor 103 senses, for example, positions of trays (e.g., trays T1 to T3 illustrated in FIG. 10). The sensor 103 may determine whether the arm unit 104 is holding a food, instead, or may be another sensor. The sensor 103 may be the imaging unit 11 included in the multispectral camera 10, instead. That is, the robot 100 and the multispectral camera 10 may be integrated with each other. It can be said that the multispectral camera 10 is incorporated into the robot 100. The robot 100 may thus be configured to obtain one or more spectra corresponding to each of one or more foods through imaging, the one or more spectra being a result of measurement of each of the one or more foods using a spectral camera.

The arm unit 104 moves foods under the control of the control unit 102. In the present embodiment, the arm unit 104 grasps and moves foods. The arm unit 104 is a six-axis robot arm, but is not limited to this. The arm unit 104 need not necessarily grasp and move foods. For example, the arm unit 104 may move a food while holding a food by suction or just press a food, instead.

The robot 100 also includes an inverter that supplies driving power to the motors.

In the food selection system 1, the multispectral camera 10 and the robot 100 are provided, for example, in a factory where foods are selected. The food selection apparatus 30 may be provided in the factory or a place distant from the factory.

2. Operation of Food Selection System

Figure 9:
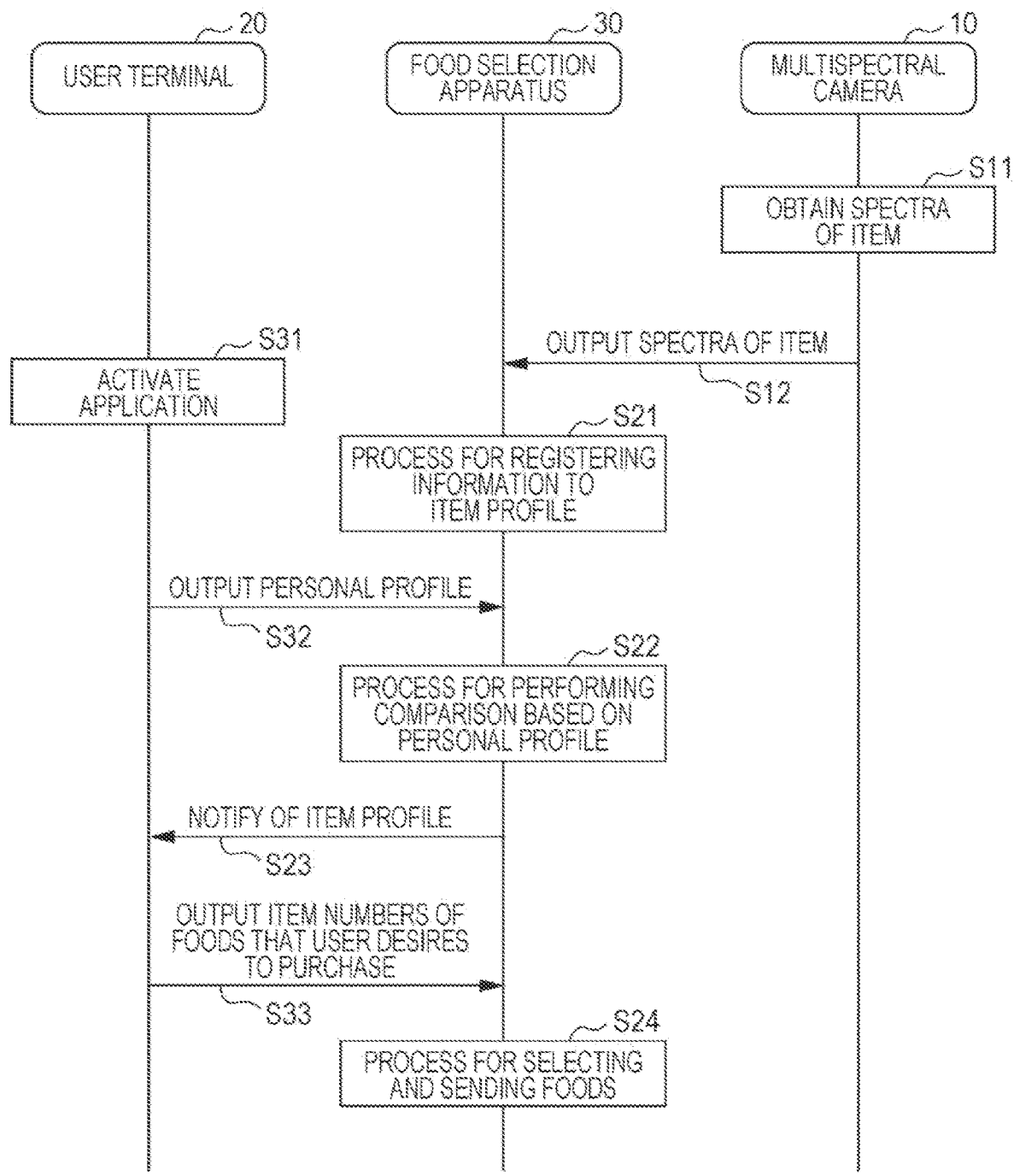
FIG. 9 is a sequence diagram illustrating an operation performed by the food selection system according to the embodiment.

First, an overall operation performed by the food selection system 1 will be described with reference to FIG. 9. FIG. 9 is a sequence diagram illustrating the operation performed by the food selection system 1 according to the present embodiment. FIG. 9 illustrates an operation at a time when new foods are delivered to the factory.

As illustrated in FIG. 9, the multispectral camera 10 measures items (foods) and obtains spectra (spectral information) regarding the item (S11). The multispectral camera 10 then outputs the obtained spectra of the item to the food selection apparatus 30 (S12).

Figure 10:
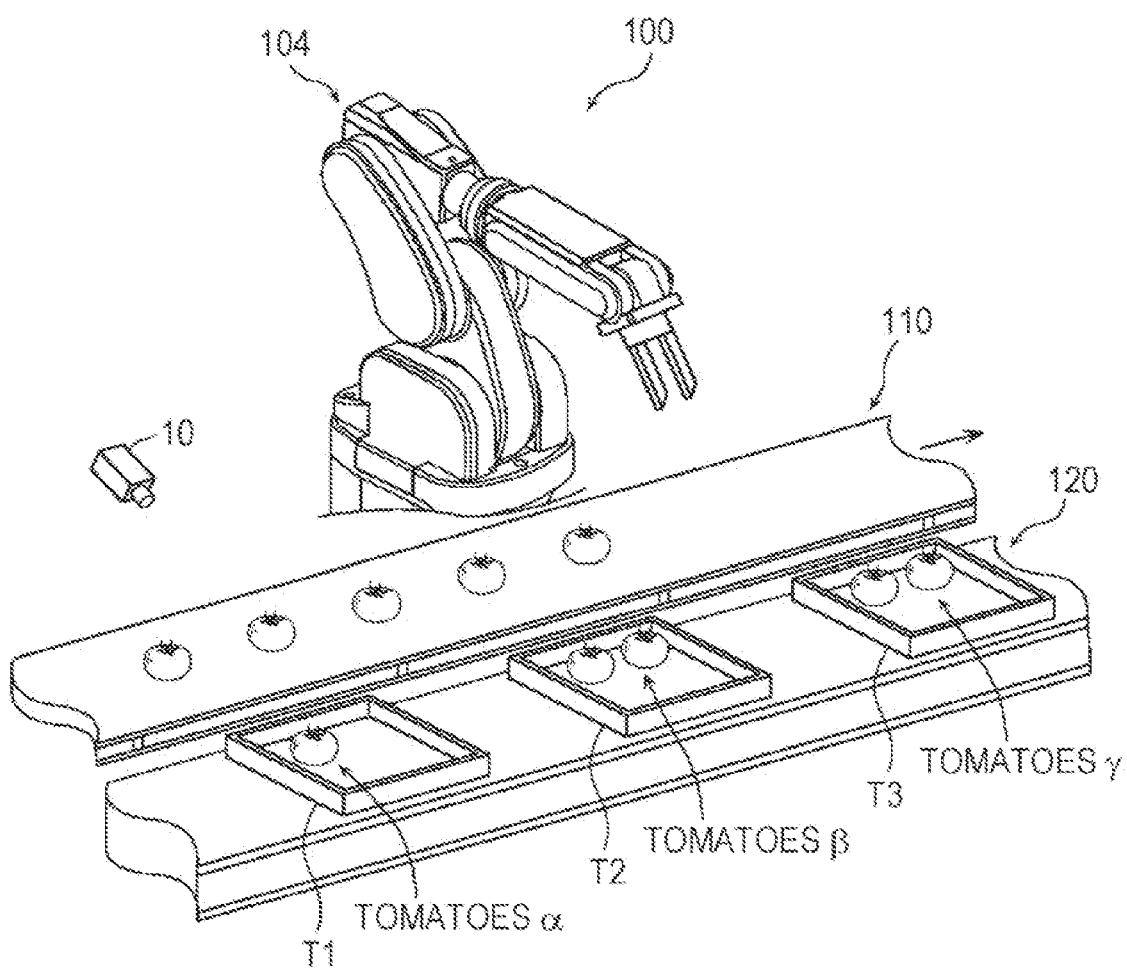
FIG. 10 is a diagram illustrating an example of how foods are sorted out.

How the robot 100 sorts out foods on the basis of spectra will be described hereinafter with reference to FIG. 10. FIG. 10 is a diagram illustrating an example of how foods are sorted out. FIG. 10 illustrates how the robot 100 handles newly delivered foods in the factory, for example, on the basis of spectra obtained by the multispectral camera 10. That is, FIG. 10 illustrates how the robot 100 sorts out foods in the factory in accordance with states of the foods. In FIG. 10, the robot 100 handles tomatoes α, β, and γ illustrated in FIG. 7.

As illustrated in FIG. 10, foods are sorted out in the factory using the robot 100, a conveying apparatus 110, and a food storage apparatus 120. The food selection system 1 may also include the conveying apparatus 110 and the food storage apparatus 120. In this case, the conveying apparatus 110 and the food storage apparatus 120 are communicably connected to the food selection apparatus 30 over the network 40. The control unit 32 may generate control signals for controlling the conveying apparatus 110 and the food storage apparatus 120.

The multispectral camera 10 measures each of one or more foods conveyed by the conveying apparatus 110 and obtains one or more spectra corresponding to the food. For example, the multispectral camera 10 successively measures the one or more foods.

The robot 100 sorts out the one or more foods on the basis of the one or more spectra corresponding to each of the one or more foods, the one or more spectra being a result of measurement of each of the one or more food using the multispectral camera 10. More specifically, the robot 100 moves each of the one or more foods conveyed by the conveying apparatus 110 to a tray (e.g., one of the trays T1 to T3) corresponding to a state of the food based on the one or more spectra.

The conveying apparatus 110 is a so-called "conveyor belt". The conveying apparatus 110 conveys foods from upstream to downstream. The one or more foods are one or more foods that have never been measured by the multispectral camera 10 after being delivered to the factory, for example, but may be one or more foods that have been measured by the multispectral camera 10 a certain period of time before, instead.

The food storage apparatus 120 stores foods whose spectra have been obtained. For example, the food storage apparatus 120 stores foods using different trays for different item numbers. In the example illustrated in FIG. 10, the tray T1 stores a tomato α, the tray T2 stores tomatoes β, and the tray T3 stores tomatoes γ. The food storage apparatus 120 may have a function of storing foods at a certain temperature.

FIG. 9 will be referred to again. The food selection apparatus 30 obtains the spectra from the multispectral camera 10 and performs a process for registering information to the item profile P2 on the basis of the obtained spectra (S21). Details of the registration process will be described later.

The user operates the input unit 22, and the user terminal 20 activates an application (S31). The user terminal 20 receives information necessary to generate a personal profile P1 through the input unit 22. The user terminal 20 then generates the personal profile P1 on the basis of the information received through the input unit 22 and outputs the generated personal profile P1 to the food selection apparatus 30 (S32). The personal profile P1 includes information regarding the user's desires on items that the user is planning to purchase and states of the items. In step S32, the user terminal 20 outputs a personal profile P1 such as that illustrated in FIG. 2 to the food selection apparatus 30.

The food selection apparatus 30 performs a process for performing comparison based on the obtained personal profile P1 (S22). More specifically, the food selection apparatus 30 determines, on the basis of the information regarding the users desires on the items included in the personal profile P1 that the user is planning to purchase and the states of the items, whether the item profile P2 includes foods that satisfy the user's desires. If the item profile P2 includes foods that suit the user's desires, the food selection apparatus 30 notifies the user terminal 20 of the item profile P2 including information regarding the foods (S23). The item profile P2 includes information regarding presence of the foods that suit the user's desires, information regarding states of the food, an advertisement for promoting the foods, and/or the like. It can also be said that the food selection apparatus 30 presents foods that suit the user's desires. The item profile P2 may include information regarding one food or, if there are more than one food that suits the user's desires, information regarding the more than one food.

Upon obtaining the item profile P2, the user terminal 20 displays the item profile P2 on the display unit 24. If the user terminal 20 receives, from the user through the input unit 22, an operation for purchasing foods, the user terminal 20 outputs, to the food selection apparatus 30, information indicating item numbers of the foods that the user desires to purchase (S33).

Figure 11:
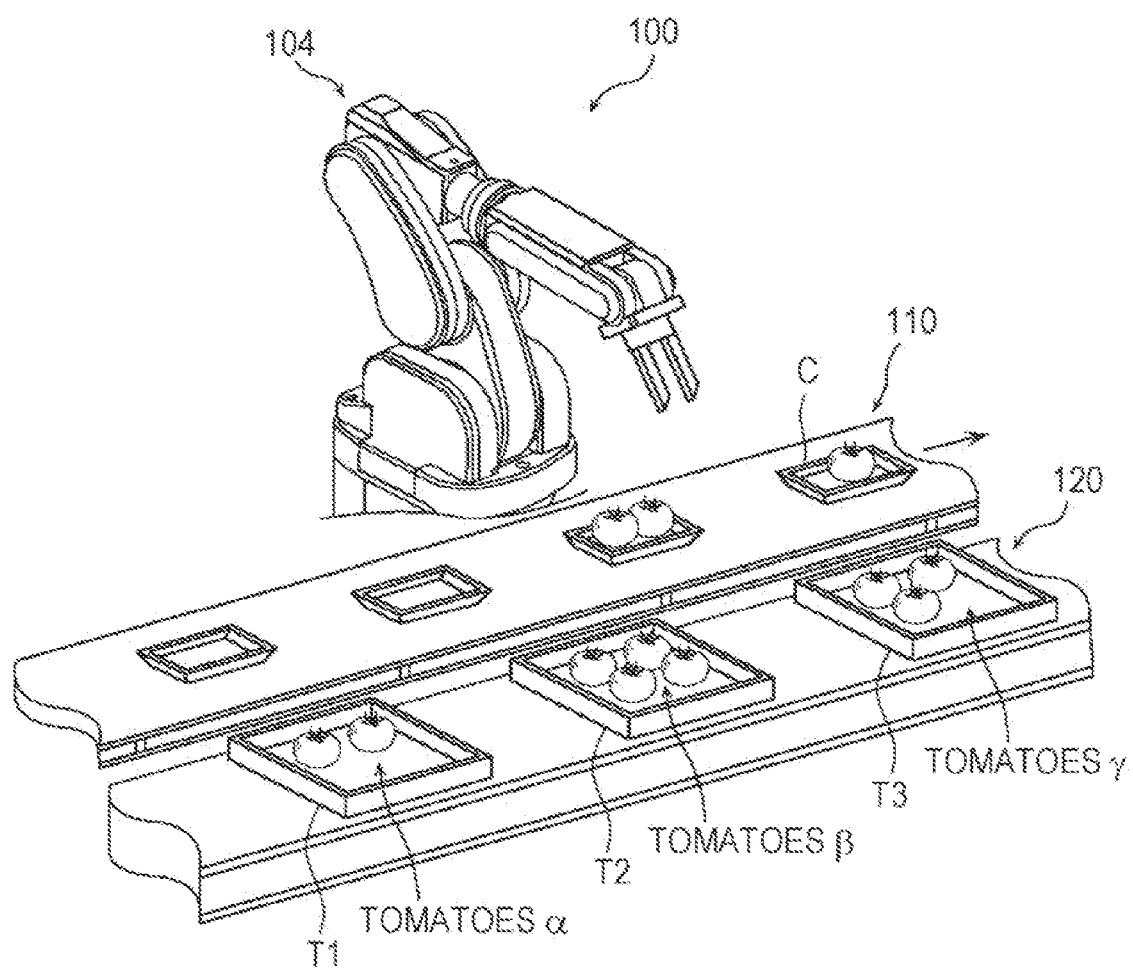
FIG. 11 is a diagram illustrating an example of how selected foods are handled.

Upon receiving the information indicating the item numbers of the foods that the user desires to purchase, that is, upon receiving an order, the food selection apparatus 30 performs a process for selecting and sending the foods (S24). FIG. 11 is a diagram illustrating an example of how foods are selected. FIG. 11 illustrates how the robot 100 handles foods in the factory that the user desires to purchase, for example, on the basis of information (hereinafter referred to as "order information") indicating item numbers of foods. That is, FIG. 11 illustrates how the robot 100 performs the operation for selecting a food in a factory. In FIG. 11, tomatoes α, β, and γ illustrated in FIG. 7 are handled. FIG. 11 does not illustrate the multispectral camera 10 and the like. The order information is an example of desire information.

As illustrated in FIG. 11, foods are selected in the factory using the robot 100, the conveying apparatus 110, and the food storage apparatus 120.

The robot 100 grasps, among one or more foods, the foods based on the order information and moves the foods to vessels C. In the example illustrated in FIG. 11, the robot 100 moves a necessary number of foods to the vessels C from the trays T1 to T3 storing the foods based on the order information.

The conveying apparatus 110 conveys the vessels C from upstream to downstream. The vessels C store the foods based on the order information.

The robot 100 thus handles, that is, selects, foods. For example, the selection of foods by the robot 100 may be included in selecting, which will be described later. The selecting may include the process for selecting a food and the operation for selecting a food.

Figure 12:
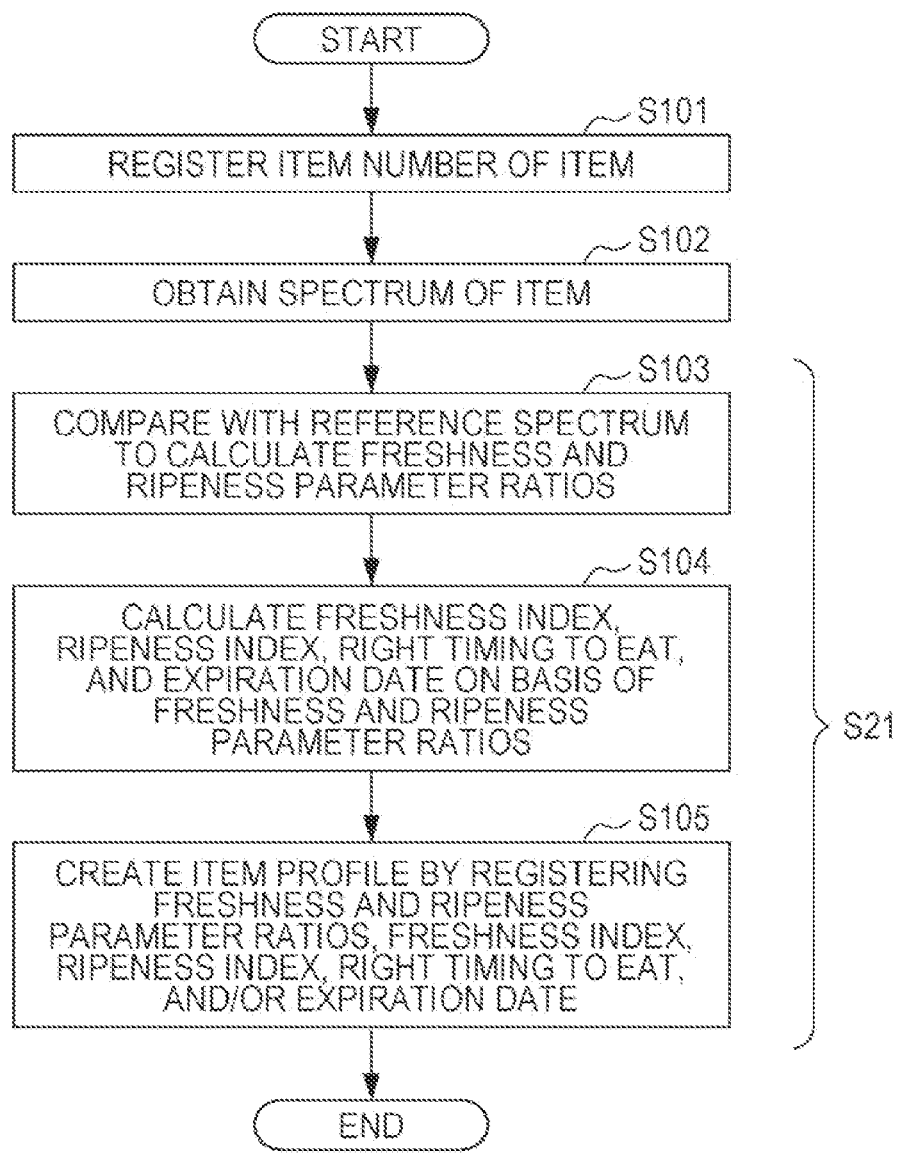
FIG. 12 is a flowchart illustrating an operation for generating an item profile in the food selection system according to the embodiment.

Next, a process for registering information to the item profile P2 performed by the food selection apparatus 30 will be described with reference to FIG. 12. FIG. 12 is a flowchart illustrating an operation for generating an item profile P2 in the food selection system 1 according to the present embodiment. The process illustrated in FIG. 12 is performed, for example, before step S111 illustrated in FIG. 13, which will be described later, is performed.

As illustrated in FIG. 12, first, the generation section 32b registers an item number of a new item (food) (S101). The generation section 32b may register an item number on the basis of, for example, information obtained from an input unit (not illustrated) included in the food selection apparatus 30 or the user terminal 20. The generation section 32b may store the item number in the storage unit 33, instead.

Next, the food selection apparatus 30 obtains a spectrum of the item from the multispectral camera 10 through the communication unit 31 (S102). In step S102, for example, the food selection apparatus 30 obtains one or more spectra corresponding to each of one or more foods, the one or more spectra being a result of measurement of each of the one or more foods using the multispectral camera 10. In step S102, for example, the food selection apparatus 30 obtains two or more spectra corresponding to each of two or more foods, the two or more spectra being a result of measurement of each of the two or more foods using the multispectral camera 10. Step S102 is an example of obtaining of one or more spectra.

The determination section 32a compares the obtained spectrum and a reference spectrum to calculate freshness and ripeness parameter ratios of the food (S103). The calculation of the freshness and ripeness parameter ratios of the food is, for example, calculation of a current freshness index and a current ripeness index of the food. In step S103, the determination section 32a may calculate at least either the freshness index or the ripeness index of the food.

Next, the determination section 32a calculates a freshness index, a ripeness index, a right timing to eat, and an expiration date on the basis of the freshness and ripeness parameter ratios calculated in step S103 (S104). The calculation of the freshness index and the ripeness index in step S104 is, for example, calculation of results of prediction of the freshness index and the ripeness index. The determination section 32a may calculate the freshness information 11 illustrated in FIG. 3 and the ripeness information 13 illustrated in FIG. 5, for example, and then calculate the right timing to eat and the expiration date on the basis of at least either the freshness information 11 or the ripeness information 13. The determination section 32a may calculate the discount information 12 in step S104, instead.

The determination section 32a may calculate at least one of the freshness index, the ripeness index, the right timing to eat, the expiration date, and a discount rate in step S104.

Next, the generation section 32b creates an item profile P2 by registering the freshness and ripeness parameter ratios, the freshness index, the ripeness index, the right timing to eat, and/or the expiration date calculated by the determination section 32a (S105). It can also be said that the generation section 32b updates the item profile P2 (adds information regarding the item newly delivered to the factory) on the basis of the various pieces of information calculated by the determination section 32a.

As a result, when a food is newly delivered to the factory, the food selection apparatus 30 can create an item profile P2 including the food. Steps S103 to S105 correspond to step S21 illustrated in FIG. 12.

Steps S101 to S105 need not necessarily be performed by the food selection apparatus 30. Steps S101 to S105 may be performed by an apparatus external to the food selection apparatus 30. The food selection apparatus 30 may then obtain an item profile P2 generated by the external apparatus over the network 40.

In this case, in a food selection method executed by the food selection apparatus 30, states of foods may be obtained on the basis of spectra obtained by measuring the foods using the multispectral camera 10, desire information indicating attributes of foods desired by the user and the states of the foods based on the spectra may be compared with each other, and a food that suits the user's desires may be selected on the basis of a result of the comparison. Alternatively, in the food selection method, a state of each of one or more foods based on one or more spectra obtained by measuring the food using the multispectral camera 10 may be obtained, desire information indicating attributes of foods desired by the user and the state of each of the one or more foods based on the one or more spectra may be compared with each other, and a food that suits the user's desires may be selected on the basis of a result of the comparison. The state of each of the one or more foods includes, for example, the freshness information 11, the discount information 12, the ripeness information 13, and/or the taste information 14.

Figure 13:
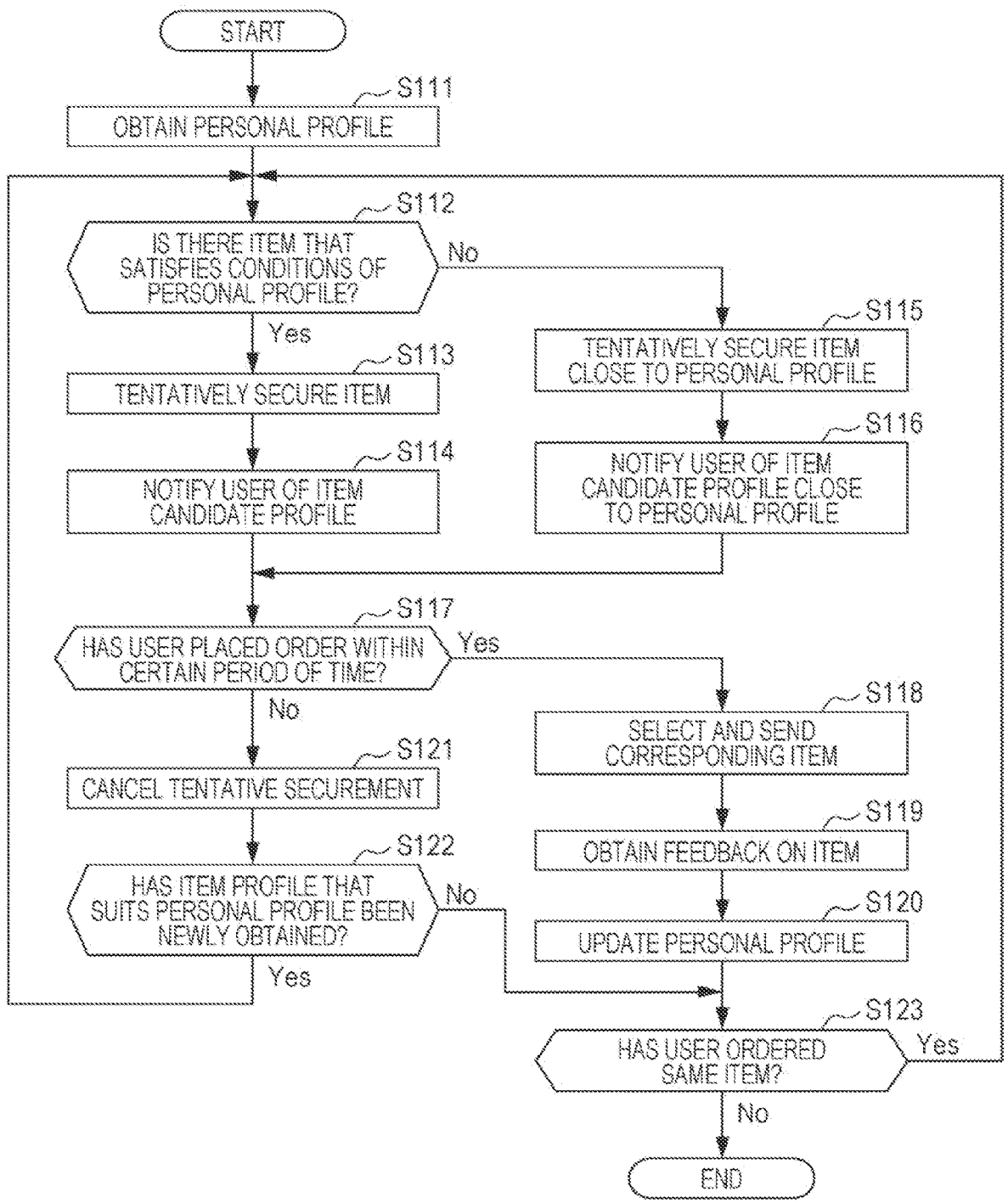
FIG. 13 is a flowchart illustrating an operation for selecting a food in the food selection system according to the embodiment.

Next, the operation for selecting a food performed in the food selection system 1 will be described with reference to FIG. 13. FIG. 13 is a flowchart illustrating the operation for selecting a food in the food selection system 1 according to the present embodiment. FIG. 13 illustrates a case where the item profile P2 is stored in the storage unit 33 in advance.

As illustrated in FIG. 13, the food selection apparatus 30 obtains the personal profile P1 from the user terminal 20 over the network 40 (S111). For example, the control unit 32 stores the personal profile P1 in the storage unit 33.

Next, the comparison section 32c determines whether there is an item that satisfies conditions of the personal profile P1 (S112). The comparison section 32c determines whether there is an item that satisfies the user's desires. More specifically, the comparison section 32c determines whether there is an item that satisfies the user's desires by comparing the conditions of the personal profile P1 and the states of the foods included in the item profile P2. The comparison section 32c then selects an item that suits the user's desires by determining whether there is an item that suits the user's desires. For example, the comparison section 32c reads a latest item profile P2 stored in the storage unit 33 and makes the determination in step S112.

The comparison section 32c makes the determination in step S112 using prediction information such as that illustrated in FIGS. 3 to 5. For example, the comparison section 32c makes the determination by comparing freshness levels and ripeness levels of items on "desired delivery date" included in the personal profile P1 and freshness levels and ripeness levels desired by the user. In other words, the comparison section 32c does not make the determination in step S112 using current freshness levels and current ripeness levels.

If the number of foods included in the item profile P2 is one, the determination in step S112 may be a determination whether the food satisfies the user's desires. If the number of foods included in the item profile P2 is more than one, the determination in step S112 may be selection, among the more than one food, of foods that satisfy the user's desires. The determination whether a food satisfies the user's desires and the selection, among more than one food, of foods that satisfy the user's desires are included in selection of foods desired by the user.

Step S112 is an example of comparing and selecting. As described above, the comparison section 32c also functions as a selector that selects a food desired by the user on the basis of a result of comparison.

The determination in step S112 will be described while taking freshness as an example with reference to FIG. 3. It is assumed that the present time is a first day and "desired delivery date" included in the personal profile P1 is the fifth day. The comparison section 32c makes the determination in step S112 by comparing a freshness level (e.g., "fresh") based on a freshness index (e.g., about 0.6) on the fifth day in the result of prediction of the freshness index illustrated in FIG. 3 and the user's preference with respect to the freshness level included in the personal profile P1.

The comparison section 32c may determine an item that satisfies all of "sweetness/sourness", "freshness", "ripeness", and "price" included in the personal profile P1 as an item that suits the user's desires or an item that satisfies at least one of "sweetness/sourness", "freshness", "ripeness", and "price" as an item that suits the user's desires. For example, the comparison section 32c may determine an item that satisfies an attribute of highest priority ("freshness" in the example illustrated in FIG. 8) in "priority" included in the personal profile P3 illustrated in FIG. 8 as an item that suits the user's desires. Satisfaction of all of "sweetness/sourness", "freshness", "ripeness", and "price" or satisfaction of at least one of "sweetness/sourness", "freshness", "ripeness", and "price" is an example of a result of comparison.

As described above, in step S112, the food selection apparatus 30 selects a food that suits the user's desires on the basis of the conditions of the personal profile P1, that is, the user's desires on foods and states of foods based on spectra obtained by the multispectral camera 10.

Next, if there is an item that suits the conditions of the personal profile P1 (Yes in S112), the comparison section 32c tentatively secures the item (S113). If there is an item that satisfies the user's desires, the comparison section 32c tentatively secures the foods. When an item is tentatively secured, the item becomes temporarily unavailable to other users for a time being. The comparison section 32c tentatively secures, for example, all pieces of the item included in the personal profile P1. Step S113 is an example of tentatively securing.

Next, the comparison section 32c notifies the user terminal 20 of an item candidate profile indicating information regarding the tentatively secured item (S114). That is, the comparison section 32c notifies the user terminal 20 of an item candidate profile indicating information regarding the selected item. The item candidate profile is an example of food information. Step S114 is an example of notifying.

Figure 14:
FIG. 14 is a diagram illustrating an example of an item candidate profile of which a user terminal is notified according to the embodiment.
Figure 15:
FIG. 15 is a diagram illustrating another example of the item candidate profile of which the user terminal is notified according to the embodiment.

For example, the comparison section 32c may output, to the user terminal 20 as the item candidate profile, information indicating that there is a food that satisfies the personal profile P1 of the user or an advertisement for an item candidate generated by the generation section 32b. For example, the generation section 32b may output an advertisement illustrated in FIG. 14 or 15 to the user terminal 20. FIG. 14 is a diagram illustrating an example of the item candidate profile of which the user terminal 20 is notified according to the present embodiment. FIG. 15 is a diagram illustrating another example of the item candidate profile of which the user terminal 20 is notified according to the present embodiment.

FIG. 14 illustrates an advertisement at a time, for example, when "item" of the personal profile P1 is "tomatoes" and "priority" is "price". The advertisement includes, for example, a reason for a discount, a discount rate, and a quantity of stock. FIG. 15 illustrates an advertisement at a time, for example, when "item" of the personal profile P1 is "melons" and "sweetness/sourness" is "1" (e.g., "Couldn't be sweeter"). An advertisement includes, for example, a sweetness/sourness level and a right timing to eat. An advertisement may also include information such as a delivery date (e.g., "Can be delivered today"). The generation section 32b generates an advertisement, for example, on the basis of the personal profile P1 and the item profile P2.

If there is no item that satisfies the conditions of the personal profile P1 (No in S112), the comparison section 32c tentatively secures, in the item profile P2, an item close to the personal profile P1 (S115). If there is no food that satisfies the user's desires, the comparison section 32c selects a food close to the user's desires as a food that suits the user's desires. The comparison section 32c then tentatively secures the food. Step S115 is another example of the tentatively securing.

An item close to the personal profile P1 is an item close to the conditions of the personal profile P1, that is, for example, an item with which at least one of attributes included in the personal profile P1 is close to the user's desire even through the attribute does not satisfy the user's desire. If "sweetness/sourness" is taken as an example and "sweetness/sourness" included in the personal profile P1 is "2", an item close to the personal profile P1 is an item whose "sweetness/sourness" is close to "2", that is, an item whose "sweetness/sourness" is "1" or "3". If "desired delivery date" is taken as an example, an item close to the personal profile P1 is an item that cannot be delivered on "desired delivery date" but can be delivered on a day after "desired delivery date".

The comparison section 32c then notifies the user terminal 20 of the item candidate profile indicating information regarding the item close to the personal profile P1 and that has been tentatively secured (S116). That is, the comparison section 32c notifies the user terminal 20 of the item candidate profile indicating information regarding the selected item. The item candidate profile is an example of food information. Step S116 is another example of the notifying.

The comparison section 32c may also notify, in step S114 or S116, the user terminal 20 of the results of prediction (prediction information) calculated by the comparison section 32c. That is, the food information may include prediction information regarding a state of the selected food. The prediction information may be, for example, graphs such as those illustrated in FIGS. 3 and 5. The food information may also include information indicating a right timing to eat the selected food based on the prediction information. The information indicating the right timings to eat may include, for example, information indicating a right timing to eat such as that illustrated in FIG. 15. The food information may also include information based on a discount rate of the food, which is based on a spectrum of the selected food. The information based on the discount rate may include, for example, a graph such as that illustrated in FIG. 4, a discount rate on "desired delivery date" included in the personal profile P1, or a price (e.g., a unit price) after the discount rate is applied.

The control unit 23 of the user terminal 20 displays, on the display unit 24, the item candidate profile of which the user terminal 20 has been notified in step S114 or S116. The control unit 23 then displays an order screen for ordering the foods on the display unit 24. FIG. 16 is a diagram illustrating an example of an order screen U1 displayed on the display unit 24 of the user terminal 20 according to the present embodiment.

As illustrated in FIG. 16, the order screen U1 includes "recommendation level", "item number", "stock", "price", "delivery date", "detailed information", and "order". The order screen U1 may also include information indicating that an item has been tentatively secured and a period of time for which an item remains tentatively secured.

"Recommendation level" indicates a degree of satisfaction of the conditions of the personal profile P1, that is, a degree of suitability to the user's desires. "Recommendation level" increases, for example, as the number of attributes included in the personal profile P1 that satisfy the user's desires increases. In addition, "recommendation level" increases, for example, as an item becomes closer to the personal profile P1.

"Item number" indicates identification information for identifying different types of food. "Item number" includes identification information corresponding to the item candidate of which the user terminal 20 has been notified in step S114 or S116.

"Stock" indicates a quantity of stock of each of types of item. The quantity of stock is, for example, the same as the number of items tentatively secured.

"Price" indicates a unit price of an item. When a discount is offered, a unit price after the discount is given is displayed. When "price" is a unit price after a discount is given, a discount rate is determined on the basis of a spectrum corresponding to a selected food. In other words, a discount rate to be applied to a price of an item selected in step S112 or the like is determined on the basis of a spectrum corresponding to the selected item.

"Delivery date" indicates a scheduled delivery date at a time when an item is ordered within a certain period of time.

"Detailed information" is used to display information regarding a state of an item indicated by "item number". When "+" shown in "detailed information" is selected, information regarding a state of an item indicated by "item number" is displayed. The information regarding a state of an item indicates freshness, ripeness, a price, a taste, and/or the like of a food and may be, for example, the information illustrated in FIGS. 3 to 6. In other words, when "+" shown in "detailed information" is selected, the food selection apparatus 30 outputs at least one of the graphs illustrated in FIGS. 3 to 6 to the user terminal 20. As a result, the user can see how freshness, ripeness, a price, a taste, and/or the like of a food will change and easily understand until when he/she can purchase an item that satisfies his/her desires (e.g., until when he/she can purchase a fresh item).

"Order" indicates information regarding an item to be ordered and includes, for example, the number of pieces of an item and a total price (total amount).

FIG. 13 will be referred to again. Next, the determination section 32a determines whether the user has placed an order within a certain period of time (S117). If the determination section 32a obtains, from the user terminal 20, information indicating that a certain item has been input on the order screen U1, the determination section 32a determines that the user has placed an order. The certain period of time is appropriately set, for example, for each food in accordance with time remaining until a right timing to eat.

Next, if the user has placed an order within the certain period of time (Yes in S117), the determination section 32a performs a process for selecting and sending a corresponding item (S118). If the item profile P2 includes a stock of the item, the update section 32d may update the stock. Step S118 is an example of delivering, which is performed to deliver an item ordered by the user.

Next, the update section 32d obtains feedback (feedback information) on the item delivered in step S118 from the user terminal 20 (S119). Step S119 is an example of obtaining feedback information regarding a food delivered to the user.

Next, the update section 32d updates the personal profile P1 stored in the storage unit 33 on the basis of the feedback (S120). The update section 32d updates items relating to the user's preference included in the personal profile P1. The update section 32d updates, for example, "sweetness/sourness" and "priority" illustrated in FIG. 2. When an item is "tomatoes" and "sweetness/sourness" is "2" and feedback indicating that the user prefers sweeter tomatoes is received from the user terminal 20 in step S120, for example, the update section 32d updates "sweetness/sourness" of the personal profile P1 from "2" to "1", which indicates higher sweetness. A fact that an item for which the feedback has been obtained is "tomatoes" and "sweetness/sourness" is "2" can be identified from a purchase history of the user. The update section 32d may update the personal profile P1 on the basis of, for example, the feedback and the purchase history. The purchase history may be stored in the storage unit 33.

As a result, the food selection apparatus 30 can select tomatoes that are closer to the user's preference and notify the user terminal 20 of the tomatoes when the user orders tomatoes next time. Step S120 is an example of updating the personal profile P1 on the basis of feedback information.

Next, the determination section 32a determines whether an order for the same item has been received from the user (S123). If the determination section 32a determines that an order for the same item has been received from the user (Yes in S123), the control unit 32 causes the process to return to step S112 and keeps performing the process. If the determination section 32a determines that an order for the same item has not been received from the user (No in S123), the control unit 32 ends the operation for selecting a food.

If the user has not placed an order within the certain period of time (No in S117), the determination section 32a cancels the tentative securement performed in step S114 or S116 (S121). As a result, the item tentatively secured by the user becomes available to other users.

Next, the determination section 32a determines whether an item profile that suits the personal profile P1 has been newly obtained (S122). If the operation illustrated in the flowchart of FIG. 12 is being performed in parallel with the operation illustrated in the flowchart of FIG. 13 and an item is newly delivered to the factory (i.e., a spectrum of an item is obtained) during a period between step S113 and step S121, the item profile P2 is updated. The determination section 32a, therefore, determines whether there is an item that suits the personal profile P1 among items obtained after step S113.

If determination section 32a determines that an item profile P2 that suits the personal profile P1 has been newly obtained (Yes in S122), the process proceeds to step S113. The item is tentatively secured, and a process in step S114 and the later steps are performed. If the determination section 32a determines that an item profile P2 that suits the personal profile P1 has not been newly obtained (No in S122), the process proceeds to step S123. Step S123 is the same as above, and description thereof is omitted.

The determination section 32a may further determine in step S122 whether an item profile close to the personal profile P1 has been newly obtained. If the determination section 32a determines in step S122 that an item profile close to the personal profile P1 has been newly obtained, the food selection apparatus 30 may cause the process to proceed to step S115 and perform a process in step S115 and the later steps.

First Modification of Embodiment

A food selection system and the like according to a first modification will be described hereinafter with reference to FIGS. 17 and 18. FIG. 17 is a diagram illustrating an example of a personal profile P4 according to the first modification. Differences from the embodiment will be mainly described hereinafter. The same components as in the embodiment will be given the same reference numerals, and description thereof might be omitted or simplified. The configuration of the food selection system according to the present modification is the same as that of the food selection system 1 according to the embodiment, and description thereof is omitted.

As illustrated in FIG. 17, the personal profile P4 stored in the storage unit 33 includes "cooking method" instead of "priority". Although FIG. 17 illustrates an example where the personal profile P4 includes "sweetness/sourness", the personal profile P4 need not include "sweetness/sourness". A cooking method desired by the user is an example of an attribute desired by the user.

In this case, in step S112 illustrated in FIG. 13, the comparison section 32c selects an item that suits the user's desires by determining whether there is an item that suits the user's desires on the basis of methods for cooking a food included in the personal profile P4. In the selecting, for example, the comparison section 32c selects a food that suits the user's desires by comparing the methods for cooking a food and a state of each of one or more foods. That is, the comparison section 32c selects a food that suits the user's desires on the basis of a result of the comparison.

If "sweetness/sourness" corresponding to "tomatoes" is "2", for example, the comparison section 32c may determine whether there are tomatoes whose "sweetness/sourness" is suitable for "salad" as a cooking method in addition to, or instead of, determining whether there are tomatoes whose "sweetness/sourness" is "2". If there are tomatoes whose "sweetness/sourness" is suitable for "salad" as a cooking method, the comparison section 32c may determine that there is an item that suits the user's desires. A food suitable for a cooking method desired by the user is an example of an item that suits the user's desire.

As a result, since the food selection apparatus 30 can select an item suitable for a cooking method, the food selection apparatus 30 can select an item that better suits the user's desires.

In addition, in this case, the user terminal 20 may be notified of an item that suits the user's desires and an item recommended on the basis of a cooking method. In other words, the display unit 24 of the user terminal 20 may display an item that suits the user's desires and an item recommended on the basis of a cooking method as illustrated in FIG. 18. FIG. 18 is a diagram illustrating an example of an item candidate profile U2 displayed on the display unit 24 of the user terminal 20 according to the first modification.

The user can consider which item to purchase by checking the item candidate profile U2 illustrated in FIG. 18.

Second Modification of Embodiment

A food selection system and the like according to a second modification will be described hereinafter with reference to FIG. 19. FIG. 19 is a diagram illustrating an example of an item candidate profile U3 displayed on the display unit 24 of the user terminal 20 according to the second modification. In other words, the food selection apparatus 30 notifies the user terminal 20 of the item candidate profile U3 illustrated in FIG. 19. Differences from the embodiment will be mainly described hereinafter. The same components as in the embodiment will be given the same reference numerals, and description thereof is omitted or simplified. The configuration of the food selection system according to the present modification is the same as that of the food selection system 1 according to the embodiment, and description thereof is omitted.

As illustrated in FIG. 19, the item candidate profile U3 displayed on the display unit 24 of the user terminal 20 includes "item number", "freshness", "sweetness/sourness", "right timing to eat", and "delivery frequency".

"Freshness" indicates a freshness level at "right timing to eat".

"Right timing to eat" indicates a period of time when it is desirable to eat an item. The item candidate profile U3 includes foods whose right timings to eat are at least partly different from one another. In the present modification, the item candidate profile U3 includes foods whose right timings to eat are different from one another. More specifically, the item candidate profile U3 includes "oranges α" whose "right timing to eat" is "2/1 to 2/7", "oranges β" whose "right timing to eat" is "2/8 to 2/14", and "oranges γ" whose "right timing to eat" is "2/15 to 2/21". The item candidate profile U3 thus includes information regarding different types of food, namely "oranges" in this case, whose right timings to eat are at least partly different from one another.

In this case, in step S112 illustrated in FIG. 13, for example, the determination section 32a selects different types of food (e.g., oranges) whose right timings to eat are different from one another as a food that suits the user's desires. One of the right timings to eat includes "desired delivery date" of the personal profile P1.

"Delivery frequency" indicates a frequency at which "oranges α", "oranges β", and "oranges γ" are to be delivered. "Delivery frequency" is, for example, "bulk delivery", "individual delivery", "biweekly delivery", or the like. In the example illustrated in FIG. 19, "delivery frequency" is "bulk delivery". In this case, "oranges α", "oranges β", and "oranges γ" are simultaneously delivered to the user. If the user receives "oranges α", "oranges β", and "oranges γ" on February 1, for example, it is already desirable to eat "oranges α", but it is too early to eat "oranges β" and "oranges γ". At this time, the user can eat "oranges α" in a state desired by the user. On February 8, it becomes desirable to eat "oranges β", but it is still too early to eat "oranges γ". At this time, the user can eat "oranges β" in the state desired by the user. On February 15, it becomes desirable to eat "oranges γ". At this time, the user can eat "oranges γ" in the state desired by the user.

The user can thus always eat oranges in the desired state when the display unit 24 displays the item candidate profile U3 including different types of food whose right timings to eat are different from one another. If the user orders an enough number of "oranges α" to eat throughout a period from February 1 to February 21, for example, some of "oranges α" might rot in a latter part of the period. With the food selection apparatus 30 according to the present modification, on the other hand, no oranges rot, and an effect of reducing food loss can be expected.

The personal profile P1, too, may include, for example, "delivery frequency". "Delivery frequency" is another example of the attribute desired by the user.

In this case, in step S112 illustrated in FIG. 13, the comparison section 32c selects two or more types of food whose right timings to eat are at least partly different from each other as a food that suits the user's desires. In the selecting, for example, the comparison section 32c selects two or more types of food whose right timings to eat are different from each other as a food that suits the user's desires on the basis of a result of comparison. The two or more types of food are, for example, types that fall within the same category of food (e.g., oranges) and whose right timings to eat are different from each other.

As a result, since the food selection apparatus 30 can select items whose right timings to eat are at least partly different from one another, the user can eat items in a desired state even if the items are delivered at once. With the food selection apparatus 30 according to the present modification, therefore, items that better suit the user's desires can be selected.

In step S118, the determination section 32a sends, on the basis of delivery frequencies included in the personal profile P1 (e.g., delivery frequencies indicated in the item candidate profile U3), two or more foods ordered by the user. In other words, if the determination section 32a receives an order for two or more foods in the delivering, the determination section 32a delivers the two or more ordered foods on the basis of the delivery frequencies included in the personal profile P1.

Third Modification of Embodiment

A food selection system and the like according to a third modification will be described hereinafter with reference to FIG. 20. FIG. 20 is a diagram illustrating an example of a personal profile P5 according to the third modification. Differences from the embodiment will be mainly described hereinafter. The same components as in the embodiment will be given the same reference numerals, and description thereof might be omitted or simplified. The configuration of the food selection system according to the present modification is the same as that of the food selection system 1 according to the embodiment, and description thereof is omitted.

As illustrated in FIG. 20, the personal profile P5 includes "delivery method" in addition to the items included in the personal profile P1 according to the embodiment. "Delivery method" is another example of the attribute desired by the user.

"Delivery method" includes, for example, information regarding a temperature range at a time of delivery of an item. The information regarding a temperature range may be, for example, "refrigerated", "unrefrigerated", or "frozen".

The determination section 32a performs the process for sending an item in step S118 illustrated in FIG. 13, but in the present modification, the determination section 32a performs a process for delivering an item using a delivery method according to a temperature range indicated in the personal profile P5. In other words, in the delivering, the determination section 32a delivers a food ordered by the user using a delivery method according to a temperature range corresponding to the food. The personal profile P1 may also include temperature ranges.

As a result, since an item is delivered to the user within a temperature range desired by the user, the user can receive the item within the temperature range. When an item is melons, for example, the melons are delivered to the user in a refrigerated state. The user receives the refrigerated melons and can immediately eat the melons without refrigerating the melons in a refrigerator.

Other Embodiments

Although the food selection method and the like according to one or more aspects of the present disclosure has been described on the basis of an embodiment and modifications (hereinafter also referred to as an "embodiment and the like"), the present disclosure is not limited to the embodiment and the like. The scope of the one or more aspects of the present disclosure may also include modes achieved by modifying the embodiment and the like in various manners conceivable by those skilled in the art and modes achieved by combining together components from different embodiments, insofar as the scope of the present disclosure is not deviated from.

For example, although a product (target) to be selected is a food in the embodiment and the like, the product to be selected is not limited to a food. The product need not be a food insofar as quality thereof deteriorates in a short period of time (e.g., a week, a month, etc.). For example, the product may be flowers.

Although discount information indicates a relationship between a freshness index and a discount rate in the embodiment and the like, the discount information is not limited to this. The discount information may be any type of information insofar as the information indicates a relationship between a state of a food identified from a spectrum (spectral information) obtained from a multispectral camera and a discount rate. The discount information may indicate, for example, a relationship between ripeness information and a discount rate or a relationship between a color of a surface of a food and a discount rate.

In addition, although the robot includes a six-axis robot arm in the embodiment and the like, the number of axes is not limited to this. In addition, the robot need not include an arm unit. Any robot including a movable unit capable of moving foods may be used. The robot may be an autonomous robot.

In addition, although an item is tentatively secured in step S113 or S115 illustrated in FIG. 13 in the embodiment and the like, items need not be tentatively secured. If a food selection apparatus obtains, from a user terminal, an instruction to tentatively secure an item indicated by an item candidate profile after notifying the user terminal of the item candidate profile in step S114 or S116, the food selection apparatus may tentatively secure the item.

Order in which the steps are performed in each of the flowcharts is an example for specifically describing the present disclosure, and may be changed. Some of the steps may be performed at the same time as (in parallel with) other steps, or some steps need not be performed.

Division of functional blocks in the block diagrams is an example, and more than one functional block may be achieved as a single functional block, a single functional block may be divided into different functional blocks, or some functions may be achieved by different functional blocks. Similar functions of functional blocks may be executed by a single piece of hardware or software in parallel with one another or in a time-sharing manner.

The food selection system may be achieved by the food selection apparatus, instead. That is, the food selection system may be achieved by a single apparatus. Although an example where the food selection apparatus is achieved by a single apparatus has been described, the food selection apparatus may be achieved by more than one apparatus, instead. When the food selection apparatus is achieved by more than one apparatus, the components of the food selection apparatus may be distributed among the apparatuses in any manner.

In addition, although an example where a system on the side of the store includes the food selection apparatus in the embodiment and the like, the system may also include a spectral camera. In this case, the spectral camera functions as an imaging unit that is a part of the system on the side of the store.

In addition, a communication method used between the apparatuses included in the food selection system according to the embodiment and the like is not limited to wireless communication. Wired communication may be performed between the apparatuses, instead. Wireless communication and wired communication may be combined together between the apparatuses, instead.

Some or all of the components included in the food selection system according to the embodiment and the like may be achieved by a single system large-scale integration (LSI) circuit.

A system LSI circuit is an ultra-multifunctional LSI circuit fabricated by integrating processing units on a single chip and is, more specifically, a computer system including a microprocessor, a read-only memory (ROM), and a random-access memory (RAM). The ROM stores a computer program. The microprocessor operates in accordance with the computer program, and the system LSI circuit achieves functions thereof.

An aspect of the present disclosure may be a computer program that causes a computer to perform the characteristic steps included in the food selection method. Another aspect of the present disclosure may be a non-transitory computer-readable recording medium storing the computer program. For example, the computer program may be stored in a recording medium and circulated or distributed. For example, the circulated computer program may be installed on an apparatus including another processor, and the processor executes the program to cause the apparatus to perform the above-described processes.

The food selection apparatus 30 may be achieved through software processing. When a processor executes software stored in a non-transitory recording medium (e.g., a memory), for example, the processor and peripheral apparatuses may achieve the functions of the food selection apparatus 30. When the processor executes the software stored in the non-transitory recording medium, for example, the processor and the peripheral apparatuses may perform processing relating to the food selection apparatus 30 including S21 to S24 illustrated in FIG. 9, S101 to S105 illustrated in FIG. 12, and S111 to S123 illustrated in FIG. 13.

The present disclosure can be widely used in selection apparatuses and the like that select products that suit the user's desires.

What is claimed is:

1. A method comprising:
obtaining one or more spectra corresponding one-to-one to one or more foods, each of the one or more spectra being a result of measurement of each of the one or more foods using a spectral camera;
comparing desire information indicating an attribute of a food desired by a user and a state of each of the one or more foods based on each of the one or more spectra; and
selecting a food that suits the user's desire on a basis of a result of the comparing,
wherein the state includes freshness, ripeness or freshness and ripeness,
wherein the freshness is represented as a freshness index over a period of time that is predicted based on the result of measurement, and
wherein the ripeness is represented as a ripeness index over a period of time that is predicted based on the result of measurement.

2. The method according to claim 1,
wherein, when there is no food that satisfies the user's desire in the selecting, a food close to the user's desire is selected as the food that suits the user's desire.

3. The method according to claim 2,
wherein the desire information includes priority information indicating order of priority of the attribute desired by the user, and
when there is no food that satisfies the user's desire in the selecting, a food close to the user's desire is selected as the food that suits the user's desire based on the priority information.

4. The method according to claim 1, further comprising:
notifying the user of food information regarding the selected food.

5. The method according to claim 4,
wherein in the notifying, the food information includes an item relating to a degree of suitability to the user's desires.

6. The method according to claim 4,
wherein in the notifying, the food information includes freshness, ripeness or freshness and ripeness of each of the one or more foods.

7. The method according to claim 1,
wherein the time of the measurement with the spectral camera is a first time, the freshness index indicates the freshness at a second time, the ripeness index indicates the ripeness at the second time, and the second time is later than the first time.

* * * * *